US010568923B2

(12) United States Patent
Thangavel et al.

(10) Patent No.: US 10,568,923 B2
(45) Date of Patent: *Feb. 25, 2020

(54) PLANT PARTS AND EXTRACTS HAVING ANTICOCCIDIAL ACTIVITY

(71) Applicant: Kemin Industries, Inc., Des Moines, IA (US)

(72) Inventors: Gokila Thangavel, Hosur (IN); Rajalekshmi Mukkalil, Cochin (IN); Haridasan Chirakkal, Chennai (IN)

(73) Assignee: KEMIN INDUSTRIES, INC., Des Moines, IA (US)

( * ) Notice: Subject to any disclaimer, the term of this patent is extended or adjusted under 35 U.S.C. 154(b) by 1050 days.

This patent is subject to a terminal disclaimer.

(21) Appl. No.: 14/675,180

(22) Filed: Mar. 31, 2015

(65) Prior Publication Data

US 2015/0273004 A1    Oct. 1, 2015

Related U.S. Application Data

(63) Continuation-in-part of application No. 13/928,504, filed on Jun. 27, 2013.

(60) Provisional application No. 61/664,795, filed on Jun. 27, 2012.

(30) Foreign Application Priority Data

Jan. 23, 2013    (IN) .............................. 177/DEL/2013

(51) Int. Cl.
*A61K 36/49* (2006.01)
*A61K 36/22* (2006.01)
*A61K 31/192* (2006.01)
*A61K 36/185* (2006.01)

(52) U.S. Cl.
CPC ............ *A61K 36/49* (2013.01); *A61K 31/192* (2013.01); *A61K 36/185* (2013.01); *A61K 36/22* (2013.01)

(58) Field of Classification Search
None
See application file for complete search history.

(56) References Cited

U.S. PATENT DOCUMENTS

| | | | |
|---|---|---|---|
| 2002/0019353 A1* | 2/2002 | Canning | A61K 31/7052 514/28 |
| 2003/0096050 A1* | 5/2003 | Inaoka | A21D 2/145 426/597 |
| 2010/0179151 A1 | 7/2010 | Heep et al. | |

FOREIGN PATENT DOCUMENTS

| | | |
|---|---|---|
| CN | 101744839 | 6/2010 |
| CN | 102988764 A | 3/2013 |
| EP | 0395294 | 10/1990 |
| EP | 896792 A1 * | 2/1999 |
| WO | WO 9613175 | 5/1996 |

OTHER PUBLICATIONS

Rao Zahid Abbas et al., "Anticoccidial Activity of *Curcuma longa* L. in Broilers", "Brazilian Archives of Biology and Technology", 2010, pp. 63-67, vol. 53, No. 1, Published in: Brazil.
Ali-Ashraf Aivazi et. al., "Larvicidal activity of oak *Quercus infectoria* Oliv. (Fagaceae) gall extracts against Anopheles stephensi Liston", "Parasitol Research", 2009, pp. 1289-1293, vol. 104.
Patricia Allen et al., "Dietary modulation of avian coccidiosis", "International Journal for Parasitology", 1998, pp. 1131-1140, vol. 28.
Patricia C. Allen et al., "Effects of Components of Artemisia annua on Coccidia Infections in Chickens", "Poultry Science", 1997, pp. 1156-1163, vol. 76.
Nuntana Aroonrerk et al., "Anti-inflammatory activity of *Quercus infectoria*, Glycyrrhiza uralensis, Kaempferia galanga and Coptis chinensis, the main components of thai herbal remedies for aphthous ulcer", "Journal of Health Research", 2009, pp. 17-22, vol. 23, No. 1.
Attarde et al., "Estimation of tannin content in some marketed harde Churna (terminalia chebula retz. family—combretaceae)", "International Journal of Pharmacy and Technology", 2010, pp. 750-756, vol. 2, No. 3.
Dayang Fredalina Basri et al., "In vitro antibacterial activity of galls of *Quercus infectoria* Olivier against Oral Pathogens", "Evidence-Based Complementary and Alternative Medicine", 2011, pp. 1-6, vol. 2012.
A. A. Biu et al., "Use of neem (*Azadirachta indica*) aqueous extract as a treatment for poultry coccidiosis in Borno State, Nigeria", "African Scientist", Sep. 30, 2006, pp. 147-153, vol. 7, No. 3, Published in: Nigeria, Africa.
Chandrakesan et al., "Efficacy of a herbal complex against caecal coccidiosis in broiler chickens", "Beterinarski Arhiv", Apr. 2, 2009, pp. 199-203, vol. 79, No. 2.
Robert A. Clare et al., "Major histocompatibility complex control of immunity elicited by genetically engineered *Eimeria tenella* (Apicomplexa) antigen in chickens", "Infection and Immunity", Mar. 1989, pp. 701-705, vol. 57, No. 3, Published in: US.
Noori Hassan Ghafour et al., "Determination of Some Chemical Constitutes of Oak Plants (*Quercus* spp) in the Mountain Oak Forest of Sulaimani Governorate", "Journal of Zankoy Sulaimani", 2010, pp. 129-142, vol. 13, No. 1.
T. Gokila, "Coccidiosis in vitro trial II", "Lab Record GT", Sep. 16, 2011, pp. 104-110.
T. Gokila, "In vitro screening of plant extracts for antisporozoidal activity—Part II", Dec. 4, 2011, p. 118.
T. Gokila et al., "In Vivo Screening of Plant Extracts for Anticoccidial Activity—Part II", "K Source WP-12-00017", 2012.

(Continued)

Primary Examiner — Terry A McKelvey
Assistant Examiner — Catheryne Chen
(74) Attorney, Agent, or Firm — Nyemaster Goode P.C.

(57) ABSTRACT

Methods of administering a composition that comprises plant extracts selected from the group consisting of *Quercus infectoria*, *Rhus chinensis* and *Terminalia chebula* containing compounds such as gallic acid, derivative of gallic acid, gallotannins and hydrosable tannins, which have been found to control coccidiosis in poultry and, more specifically, coccidiosis caused by *Eimeria* spp. The plant extracts result in a reduction of lesion score, oocysts per gram of fecal matter and mortality.

12 Claims, 20 Drawing Sheets

(56) References Cited

OTHER PUBLICATIONS

Sam Hur et al., "Effects of Feeding Condensed Tannin-containing Plants on Natural Coccidian Infection in Goats", "Asian-Australian Journal of Animal Sciences", Sep. 1, 2009, pp. 1262-1266, vol. 18, No. 9.

Jang et al., "Anticoccidial effet of green tea-based diets against Eimeria maxima", "Veterinary Parasitology", Oct. 5, 2006, pp. 172-175, vol. 144.

S.H.M. Jeurissen et al., "Eimeria tenella infections in chickens: aspects of host-parasite: interactions", "Veterinary immunobiology and immunopathology", 1996, pp. 231-238, vol. 54.

Gurpreet Kaur et al., "*Quercus infectoria* galls possess antioxidant activity and abrogates oxidative stress-induced functional alterations in murine macrophages", "Chemico-Biological Interactions", 2008, pp. 272-282, vol. 171.

Manouchehr Khazandi et al., "Developing an in vitro method for Eimeria tenella attachment to its preferred and non-preferred intestinal sites", "Experimental Parasitology", Jan. 2010, pp. 137-140, vol. 125, Published in: Australia.

Rezvan Kiani et al., "Sources and Routes of Introduction of Eimeria Oocysts into Broiler Chick's Houses", "International Study of Poultry Science", 2007, pp. 925-927, vol. 6, No. 12, Published in: Ahvaz, Iran.

Kaio Kitazato et al., "Viral infectious disease and natural products with antiviral activity", "Drug Discoveries and Therapeutics", 2007, pp. 14-22, vol. 1, No. 1.

Hyun-A Lee et al., "Anticoccidial effects of Galla rhois extract on Eimeria tenella-infected chicken", "Laboratory Animal Research", 2012, pp. 193-197, vol. 28, No. 3.

T. Leela et al., "Studies of the Antibacterial Activity of *Quercus infectoria* Galls", "International Conference on Bioscience, Biochemistry and Bioinformatics IPCBEE", 2011, pp. 410-414, vol. 5.

M.E.E. McCann et a., "The Use of Mannan-Oligosaccharides and/or Tannin in Boiler Diets", "Internatioal Journal of Poultry Science", 2006, pp. 873-879, vol. 5, No. 9.

McDougald et al., "Enhancement of Resitance to Coccidiosis and Necrotic Enteritis in Broiler Chickens by Dietary Muscandine Pomace", "Avian Diseases", 2008, pp. 646-651, vol. 52.

Abdul Lateef Molan et al., "Effect of pine bark (*Pinus radiata*) extracts on sporulation of", "Folia parasitologica", 2009, pp. 1-5, vol. 56.

V. Naidoo et al., "The value of plant extracts with antioxidant activity in attenuating coccidiosis in broiler chickens", "Veterinary Parasitology", 2008, pp. 214-219, vol. 153.

N.E. Nweze et al., "Anticoccidial effects of Ageratum conyzoides", "Journal of Ethnopharmacology", 2009, pp. 6-9, vol. 122.

Ojha et al., "Antioxidant Activity of Andrographis paniculata in Ischemic Myocardium of Rat", "Global Journal of Pharmacalogy", 2009, p. 154-157, vol. 3, No. 3.

Y. B. Rajeshwari et al., "Efficacy of DIAREX VET in Treating Rabbit Coccidiosis", "The Veterinarian", 2003, pp. 12-13, vol. 27.

Simone Rochfort et al., "Plant bioactives for ruminant health and productivity", "Phytochemistry", 2008, pp. 299-322, vol. 69.

Vongyao Sawangjaroen et al, "The effects of extracts from anti-diarrheic Thai medicinal plants on the in vitro growth of the intestinal protozoa parasite: Blastocystis hominis", "Journal of Ethnopharmacology", 2005, pp. 67-72, vol. 98.

Nongyao Sawangjaroen et al, "Effects of Piper longum fruit, Piper sarmentosum root and *Quercus infectoria* nut gall on caecal amoebiasis in mice", "Journal of Ethnopharmacology", 2004, pp. 357-360, vol. 91.

Soon et al., "Ultrastructural Findings and Elemental Analysis of *Quercus infectoria* Oliv", "Annals of Microscopy", 2007, pp. 32-37, vol. 7.

Suryaprakash et al., "Pharmacological Review on Terminalia chebula", "International Journal of Research in Pharmaceutical and Biomedical Sciences", 2012, pp. 679-683, vol. 3, No. 2.

M. L. Wang et al., "Influence of Grape Seed Proanthocyanidin Extract in Broiler Chickens: Effect on Chicken Coccidiosis and Antioxidant Statue", "Poultry Science", 2008, pp. 2273-2280, vol. 87.

R.B. Williams, "Intercurrent coccidiosis and necrotic enteritis of chickens: Rational, integrated disease management by maintenance of gut integrity", "Avian Pathology", Jun. 2005, pp. 159-180, vol. 34, No. 3.

G.F. Zhang et al., "Effects of ginger root (*Zingiber officinale*) processed to different particle sizes on growth performance, antioxidant status, and serum metabolites of broiler chickens", "Poultry Science", 2009, pp. 2159-2166, vol. 88, Published in: China.

\* cited by examiner

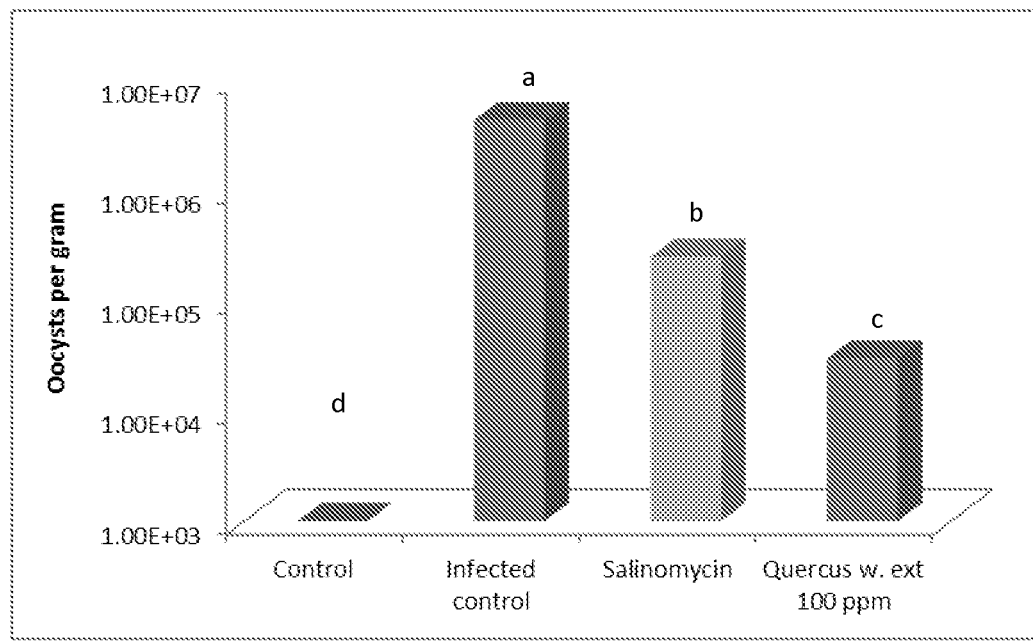
FIG. 5    n = 3, p<0.05
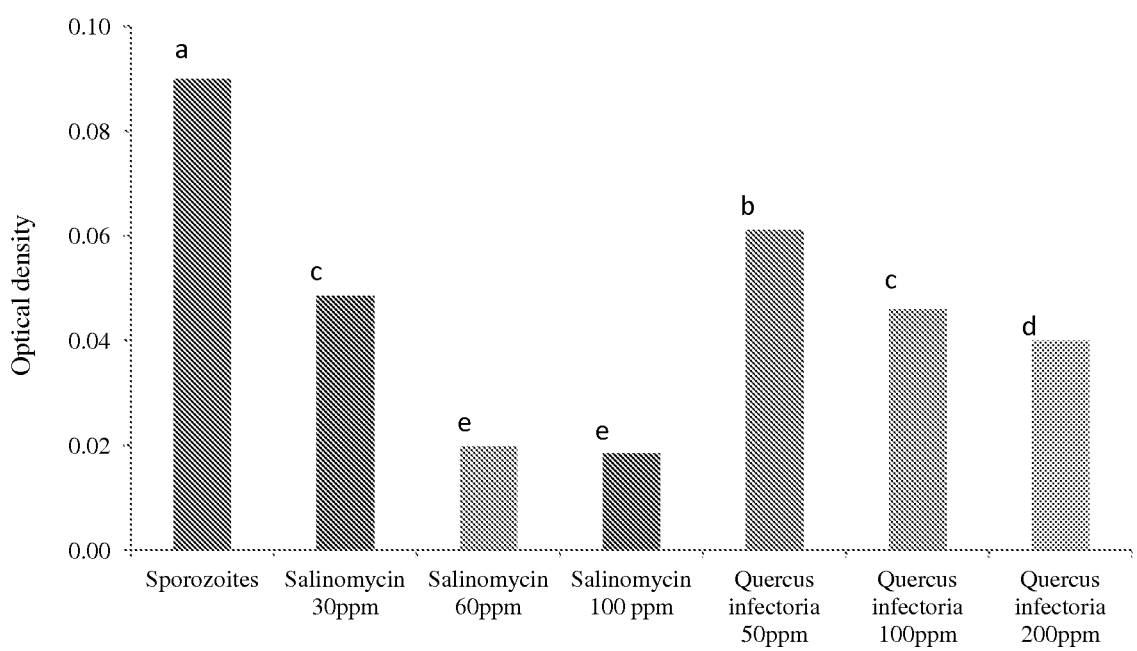
FIG. 6    n = 3, p<0.05

US 10,568,923 B2

PLANT PARTS AND EXTRACTS HAVING ANTICOCCIDIAL ACTIVITY

This application is a continuation-in-part application of U.S. patent application Ser. No. 13/928,504, filed Jun. 26, 2013, which claims priority to U.S. Patent Application Ser. No. 61/664,795, filed Jun. 27, 2012 and Indian Application No. 177/DEL/2013, filed Jan. 23, 2013, both of which are incorporated herein by this reference.

BACKGROUND OF THE INVENTION

The present invention relates generally to the control of coccidiosis and, more specifically, to the application of plant parts, plant extracts and compounds to control coccidiosis in poultry and other animals.

Coccidiosis is a major disease in the poultry industry and according to a recent survey, it is estimated that the global impact is greater than $3 billion USD annually (worldpoultry.net/Broilers/Health/2009/9/In-ovo-vaccination-against-coccidiosis-WP006949W/—accessed Jun. 18, 2013). Coccidiosis is caused by a protozoan parasite, namely *Eimeria*, belonging to the phylum Apicomplexa, and the family Eimeriidae (Clare, R. A and Danforth, H. D (1989). Major histocompatibility complex control of immunity elicited by genetically engineered *Eimeria tenella* (Apicomplexa) antigen in chickens. *Infection and immunity*, 57 (3): 701-705). The parasite invades the gut cells and causes necrosis in the intestine which leads to malabsorption, diarrhea, morbidity, reduction of weight gain, poor feed conversion, and, in severe cases, mortality (Williams, R. B (2005). Intercurrent coccidiosis and necrotic enteritis of chickens: Rational, integrated disease management by maintenance of gut integrity. *Avian Pathology*, 34(3), 159-180). Seven different species of *Eimeria*, *E. acervulina*, *E. brunetti*, *E. maxima*, *E. mitis*, *E. necatrix*, *E. praecox*, and *E. tenella* are known to cause coccidiosis in poultry (Williams, 2005) and the species are highly host and site specific. *E. tenella* is one of the major species causing coccidiosis in poultry, and their site of infection is the caecum (Khazandi, M and Tivey, D (2010). Developing an in vitro method for *Eimeria tenella* attachment to its preferred and non-preferred intestinal sites. *Experimental Parasitology*, 125 (2), 137-140). Coccidiosis is currently controlled by medication, but the increasing emergence of drug-resistant strains of *Eimeria* requires the development of an alternative control strategy. Since plants are known to possess antiparasitic and anticoccidial activity due to the presence of phenolic compounds (Tipu, M. A., Akhtar, M. S., Anjum, M. I and Raja, M. L (2006). New dimension of medicinal plants as animal feed. *Pakistan vet. J.*, 26(3): 144-148), they could be potential sources of bioactive molecules against coccidiosis in poultry.

Others have attempted to use plant parts or plant extracts in treating coccidiosis. For example, McCann et al. tested the effect of Sweet Chestnut Wood tannins on the performance of broiler chicks vaccinated with a live coccidia vaccine (M. E. E. McCann, E. Newell, C. Preston and K. Forbes. The Use of Mannan-Oligosaccharides and/or Tannin in Broiler Diets. Intl. J. of Poultry Sci. 5 (9): 873-879, 2006). They reported that supplementation with mannan-oligosaccharides or tannins, either individually or in combination, did not reduce the impact of the coccidiosis.

Wang et al. teach the use of a grape seed proanthocyanidin extract on coccidiosis (Wang, et al. Influence of Grape Seed Proanthocyanidin Extract in Broiler Chickens: Effect on Chicken Coccidiosis and Antioxidant Status. Poultry Science. 87:2273-2280, 2008). They attributed activity to the anti-inflammatory and antioxidant properties of the proanthocyanidins, a condensed tannin rather than a hydrolysable tannin.

Naidoo et al. teach an in vivo study using four plants selected based on their antioxidant activity (Naidoo et al. The value of plant extracts with antioxidant activity in attenuating coccidiosis in broiler chickens. Veterinary Parasitology. 153:214-219; 2008). They observed that one of the plants (*Tulbaghia violacea*) reduced the *Eimeria* oocyst counts in the chicken excreta and they speculate that this effect could be due to the antioxidant compound S (methylthiomethyl) cysteine sulfoxide.

McDougald et al. describe the use of a muscadine pomace to enhance resistance to coccidiosis in broiler chickens (McDougald et al. Enhancement of Resistance to Coccidiosis and Necrotic Enteritis in Broiler Chickens by Dietary Muscadine Pomace. Avian Diseases. 52: 646-651; 2008). Muscadine pomace is a by-product of grapes used in wine production. They make no mention of efficacy of any specific compounds in the pomace. The proposed anticoccidial activity differs significantly from the activities proposed by Wang et al. and Naidoo et al.

SUMMARY OF THE INVENTION

The present invention consists of the identification and use of plant parts and plant extracts effective in the control of coccidiosis in animals, particularly in poultry. Specifically, plant parts and natural extracts of *Quercus infectoria*, *Rhus chinensis* gall nut, *Terminalia chebula* fruit have been found to control coccidiosis in poultry and, more specifically, coccidiosis caused by *Eimeria* spp. More specifically, plant parts or extracts containing efficacious amounts of compounds selected from the group consisting of gallic acid, gallotannins and hydrolysable tannins.

The plant parts and natural extracts of gall nuts of *Quercus infectoria*, *Rhus chinensis* and fruits of *Terminalia chebula* result in a reduction of lesion score, oocysts per gram of fecal matter and mortality. The plant parts/extract was also found to have a direct inhibitory effect on the sporozoites of *Eimeria*, as observed in the in vitro MTT assay. Compounds selected gallic acid, gallotannins and hydrolysable tannins were also found to reduce lesion score, oocysts per gram of fecal matter and mortality. The compounds were also found to have a direct inhibitory effect on the sporozoites of *Eimeria*, as observed in the in vitro MTT assay.

The present invention also consists of a method of controlling coccidiosis in poultry and other animals by administering a composition comprising plant parts or extracts of plants containing an efficacious amount of gall nuts of *Quercus infectoria*, *Rhus chinensis*, *Terminalia chebula* fruit and/or compounds such as gallic acid, gallotannins and hydrolysable tannins.

BRIEF DESCRIPTION OF THE DRAWINGS

FIG. 5 is a chart of the oocysts per gram (OPG) of excreta of birds treated with *Q. infectoria* water extract on day 7 post infection; columns with different superscripts are statistically significant (p<0.05).

FIG. 6 is a chart of the MTT assay carried out for the evaluation of *Q. infectoria* at various dosage levels along with a coccidiostat (Salinomycin) as positive control; columns with different superscripts are statistically significant (p<0.05).

DESCRIPTION OF THE INVENTION

Figure 1:
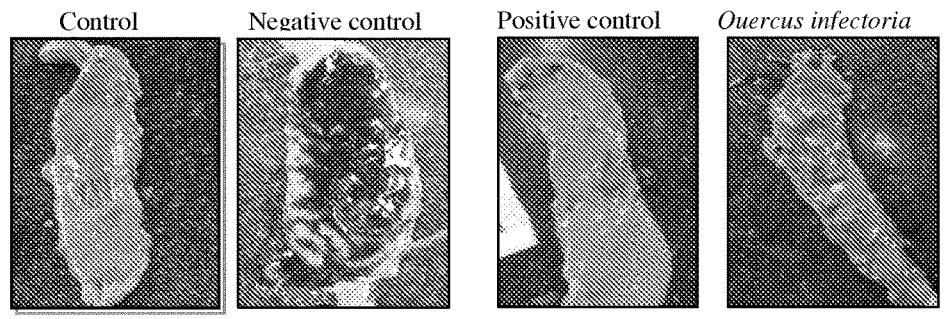
FIG. 1 is an image of caecal lesions of birds treated with *Quercus infectoria*

A preliminary in vivo evaluation of crude powder of *Q. infectoria* gall nuts (100-800 micron particle size, procured from Pooja Herbs, Mumbai, India) in controlling coccidiosis at 100 g/ton of feed dose gave some indication of promising results which urged further evaluation at higher dosage. A 35 day in vivo trial conducted in broiler birds challenged with oocysts of *Eimeria tenella* showed that *Q. infectoria* gall nuts reduced the lesion score to 0 and mortality to 0%, comparable to the positive control (0%), whereas the negative control showed a score of 4 and a mortality of 17%. The histopathological analysis of the caecum samples showed that the birds treated with *Q. infectoria* showed lesser area infected by the parasite, lower mononuclear infiltrations and hemorrhages of the caecum.

In general in this description, a plant part, extract or compounds is termed to be efficacious if it can result in statistically significant reduction in the lesion score, the oocysts shed in the excreta, (Oocyst Per Gram (OPG)) or the mortality of the birds as compared to the infected control which is untreated. Generally, administration of gallic acid and gallic acid containing formulations are described with formulations providing a dosage from 0.1 to 50 ppm, preferably from 2 to 20 ppm, and most preferably from 3 to 10 ppm through feed or water or an equivalent supplementation through other routes. The plants, plant parts and/or extracts described contain around a minimum of 0.1% of gallic acid.

The efficacy of *Q. infectoria* crude powder in controlling mixed infection of *Eimeria* in broiler birds was evaluated. The results showed that there was significant reduction in the lesion score for E. tenella and E. acervulina as compared to the infected control and even the positive control, Salinomycin. Whereas in case of E. maxima, a numerical reduction in the lesion score was observed as compared to the infected control and Salinomycin. The oocysts per gram of treated groups were significantly lower than the infected control and Salinomycin group, however, mortality was not observed in any of the treatment groups including the infected control. This proves the efficacy of Q. infectoria in controlling coccidiosis caused by other species of Eimeria. Further, to determine the mode of action of Q. infectoria, an in vitro method based on 3-(4, 5-Dimethyl-2-thiazolyl)-2,5-diphenyl-2H-tetrazolium bromide (MTT) reduction assay was developed to evaluate the anti-sporozoite activity of plant extracts as a measure of the viability of the sporozoites. Studies with Q. infectoria gall nut on the sporozoites of Eimeria tenella showed significant reduction in the viability of sporozoites compared to the sporozoite control. A dose dependent efficacy was observed in studies conducted with different dosages of Q. infectoria and the results were validated by conducting experiments several times independently. Hence, direct anti-sporozoite activity of Q. infectoria could be one of the modes of actions which attributes to the efficacy of the extract in controlling in coccidiosis in vivo.

Similarly, to determine the mode of action of Q. infectoria in controlling Eimeria in a host cell line, an in vitro assay was developed based on a co-culture of host cells and Eimeria parasites. Cells and parasite are combined in an assay with a positive control and different test products. The invasion and proliferation of the Eimeria parasites is measured by detecting Eimeria DNA using real-time PCR. For this, specific primers were selected and PCR conditions were optimised. The positive control and potential anticoccidial compounds are added to the in vitro assay in three different ways:

The products are combined with Eimeria sporozoites and added to the host cells.

The products are added to the sporozoites for a specific time, then removed and afterwards the sporozoites are added to the host cells.

The products are added to the host cells for a specific time, then removed and afterwards the sporozoites are added to the host cells.

The effect of Quercus infectoria was evaluated in the in vitro assay.

Example 1—Efficacy of Quercus Infectoria in Controlling Caecal Coccidiosis

Experimental Facility and Study Design.

The screening trial was conducted at a poultry farm facility located in Gummidipundi, India. Straight run commercial hybrid broiler chickens, Gallus domesticus (Var. Vencobb 400) were used for the study. Day old male chicks were procured, weighed individually, wing banded, and randomly segregated into groups. The experimental design is detailed in Table 1.

TABLE 1

Study design.

| Category | Trial Parameter |
| --- | --- |
| Rearing type | Cages |
| Age of birds at the start of the trial | 1 day old |

TABLE 1-continued

Study design.

| Category | Trial Parameter |
| --- | --- |
| Total no of Birds | 56 |
| Number of groups | 8 |
| No of birds/groups | 7 |
| Duration of the trial | 35 days |

Farm Management.

Good farm managing practices were followed during the trial. The entire farm and the equipment used for the study were cleaned and disinfected before the arrival of the chicks. The birds were housed in cages organized on concrete flooring and a tray was provided at the bottom of the cages to facilitate collection of fecal samples. The temperature and humidity of the farm was monitored continuously.

Vaccination Schedule.

The birds were vaccinated for Newcastle Disease Virus (NDV) and Infectious Bursal Disease (IBD).

Feed Formulation.

A corn soya based mash diet was formulated. The feed ingredients were procured from Ponni feeds, Tamil Nadu, India. The mash feed was fed ad libitum to the birds throughout the study period. Three feed formulations were prepared according to the phases of the life of the bird; Prestarter (Day 1-10), Starter (Day 11-20), and Finisher feed (Day 21-42). No antimicrobials and supplements were used in the feed formulation.

Details of Treatment Groups.

Groups and the treatments are shown in Table 2. The treated birds were fed with plant extract incorporated in the feed from day 1 (Table 2). The crude powders of Q. infectoria gall nut were procured from Pooja herbs, Mumbai, India.

TABLE 2

Details of treatment groups and feed.

| Groups | Treatments |
| --- | --- |
| Control 1 (uninfected control) | Normal feed |
| Control 2 (Negative infected Control) | Coccidiosis induction + Normal feed |
| Control 3 (Positive Control) | Coccidiosis induction + Feed with Coxistac* at 1000 g/ton |
| Treatment | Coccidiosis induction + Feed with Q. infectoria at 100 g/ton |

*Coxistac is a product from Pfizer containing Salinomycin at 12% concentration. Hence, addition of Coxistac at the mentioned dose of 500 g/ton of feed will enable delivery of Salinomycin at 60 ppm levels in the feed which is the recommended preventive dose for broilers. The dose in this experiment was double the recommended concentration.

Induction of Coccidiosis.

Sporulated oocysts of E. tenella (Houghton strain [Chapman, H. D. and Shirley, M. W. 2003. The Houghton strain of Eimeria tenella: A review of the type strain selected from genome sequencing. Avian Pathol., 32: 115-127]-propagated) were orally administered to each bird on day 14, 15 and 16 of age through oral gavage at a dose of $1 \times 10^5$ oocysts/bird/day. Feeding was stopped on the day of inoculation, for 2 h before and 2 h after inoculation.

Parameters Analyzed.

The parameters that were chosen for analyses were the indices of pathogenesis namely excreta appearance, mortality, lesion scoring of the caecum for coccidiosis, and oocysts per gram (OPG) of excreta. The methods are detailed below.

Examination of Excreta.

The excreta of the birds were monitored daily from the day 1 post infection to day 10 for their consistency, presence of blood, mucus, undigested feed, and orange color. Scoring of the excreta was carried out based on the severity of blood shedding.

Mortality.

The mortality of the birds was recorded on a daily basis and post mortem was carried out to confirm the cause of death.

Lesion Scoring of the Caecum.

On day 5 and 7 post infection, 2 birds from each of the groups were sacrificed by cervical dislocation and the intestine was cut open. The caeca of the birds were scored for coccidiosis lesions. The scoring was done based on the severity of the lesions in the caecum and the presence of blood (Johnson, J. K., and W. M. Reid. (1970). Anticoccidial drugs: lesion scoring techniques in battery and floor-pen experiments with chickens. Experimental Parasitology 28:30-36). The score for caecal coccidiosis was a scale of 0-4.

OPG of Excreta.

Triplicate samples of the excreta of the birds were collected randomly from the tray kept below the cages and the oocyst per gram was evaluated.

Results

Indices of Pathogenesis.

The observations on the excreta of the birds showed that the blood shedding in the infected groups started by day 4 post infection and the severity peaked on the day 5. The results of the scoring of the excreta are given in Table 3. Day 7 post infection the excreta were found to be normal with no blood. The positive control (C3, Table 3) on day 5 had a score of 3 as compared to the negative control (C2, Table 3) of 4. Birds treated with Q. infectoria had a lower score of 2 and were better than the positive control.

TABLE 3

Scoring of excreta on day 5 post infection.

| Treatments | Score | Description |
|---|---|---|
| C1 - uninfected control | 0 | Excreta normal consistency |
| C2 - Negative infected control | 4 | Presence of heavy raw blood |
| C3 - Positive Control | 3 | Excreta with blood +++ |
| T - Q. infectoria at 100 g/ton | 2 | Excreta with blood ++ |

+ denotes the severity of blood loss and amount of blood in the excreta.

Lesion Scoring of the Caecum.

Lesion scoring of the caeca on day 5 and 7 post infection indicated that the lesions were severe on day 5, and the birds started recovering on day 7 post infection which was indicated by the formation of a caecal plug. This followed the normal pattern of infection enabling the removal of oocysts from the caeca. The results of the lesion score showed that the positive control (Salinomycin control did not show any difference in the score as compared to the negative control due to inexplicable reasons. The treatment with Q. infectoria reduced the lesion score as compared to the negative control (Table 4). The reduced lesion score correlated with reduced excreta score and absence of mortality.

TABLE 4

Lesion score of the caeca on day 5 post infection

| Treatments | Lesion Score |
|---|---|
| C1 - uninfected control | 0 |
| C2 - Negative infected control | 3 |
| C3 - Positive Control | 3 |
| T - Q. infectoria at 100 g/ton | 2.5 |

OPG of Excreta of the Birds on Day 7 Post Infection.

The counts of OPG of excreta of the birds on day 7 post infection are shown in Table 5. Unexpectedly, the anticoccidial Salinomycin treated birds (C3, Table 5) did not show any indication of reduction of oocysts as compared to the C2 (Table 5). The values presented are an average of three replicates.

TABLE 5

Oocysts per gram of excreta on day 7 post infection

| Treatments | Average Oocysts Per Gram Excreta | CV |
|---|---|---|
| C2 - Negative infected control | 2.5E+05 | 1.23 |
| C3 - Positive Control | 4.0E+05 | 0.68 |
| T - Q. infectoria at 100 g/ton | 3.5E+05 | 1.36 |

Mortality.

The rate of mortality was 17% in control 2 (negative infected control). There was no mortality in other groups. The lesion score and OPG data of the positive control did not show any difference from that of the negative control.

Although the positive control did not perform well in this trial, the lesion scores of birds treated with plant extracts of Q. infectoria were lower than the negative infected control which indicates that they could be candidates for further investigation. However, they showed no reduction in the OPG.

Example 2—Efficacy of Quercus Infectoria in Controlling Caecal Coccidiosis

A 35 day in vivo challenge trial was conducted in broiler birds challenged with Eimeria tenella The treatment groups included, 1) control, uninfected normal birds; 2) negative control, birds infected with E. tenella and fed normal diet without any anticoccidial compounds; 3) positive control, birds infected and fed diet containing Coxistac (anticoccidial agent, Salinomycin) at the recommended dose of 500 g/ton and 4) treatment group including infected birds administered diet containing Q. infectoria gall nut at 500 g/ton dose. No mortality was observed in the positive control group and treatment group supplemented with crude powder of gall nuts of Quercus infectoria. The caecal lesions indicated that the negative control birds were highly infected with an average score of 4 whereas the positive control had score of 0. Birds treated with Quercus infectoria showed results similar to the positive control (0). Q. infectoria showed reduction in the OPG counts comparable to the positive control. The histopathological analysis of the caecum samples showed that the birds treated with Q. infectoria had lesser area affected by Eimeria, no hemorrhages and minimal mononuclear infiltrations up to the mucosa.

The second in vivo experiment involved the following treatment groups.

TABLE 6

Description of treatment groups

| Groups | Treatments |
|---|---|
| Control 1 (C1) | Uninfected control - Normal feed without anticoccidial |
| Control 2 (C2) | Negative control - Coccidiosis induction + Normal feed without anticoccidial |
| Control 3 (C3) | Positive Control - Coccidiosis induction + Normal feed with Coxistac 12% @ 500 g/ton* |
| Treatment (T) | Coccidiosis induction + Normal feed w Q. infectoria |

*Coxistac is a product from Pfizer containing Salinomycin at 12% concentration. Hence, addition of Coxistac at the mentioned dose of 500 g/ton of feed will enable delivery of Salinomycin at 60 ppm levels in the feed which is the recommended preventive dose for broilers.

Results

Caecal Lesions on Day 5 Post Infection.

The lesion scoring for caecal coccidiosis was carried out on day 5 post infection based on the criteria of scoring as before. The results of the scoring showed that the positive control completely alleviated the effects of caecal coccidiosis as compared to the negative infected control. $Q.$ $infectoria$ treated birds showed no lesions in the caecum and was comparable to the positive control and uninfected control C1 (Table 7, FIG. 1).

TABLE 7

Lesion scoring on day 5 post infection.

| Treatments | Lesion Score |
|---|---|
| C1 - Uninfected control | $0^e$ |
| C2 - Negative infected control | $4^a$ |
| C3 - Positive Control | $0^e$ |
| T - Q. infectoria | $0^e$ |

Columns with different superscripts are statistically significant ($p < 0.05$).

Oocyst Counts in Excreta.

Figure 2:
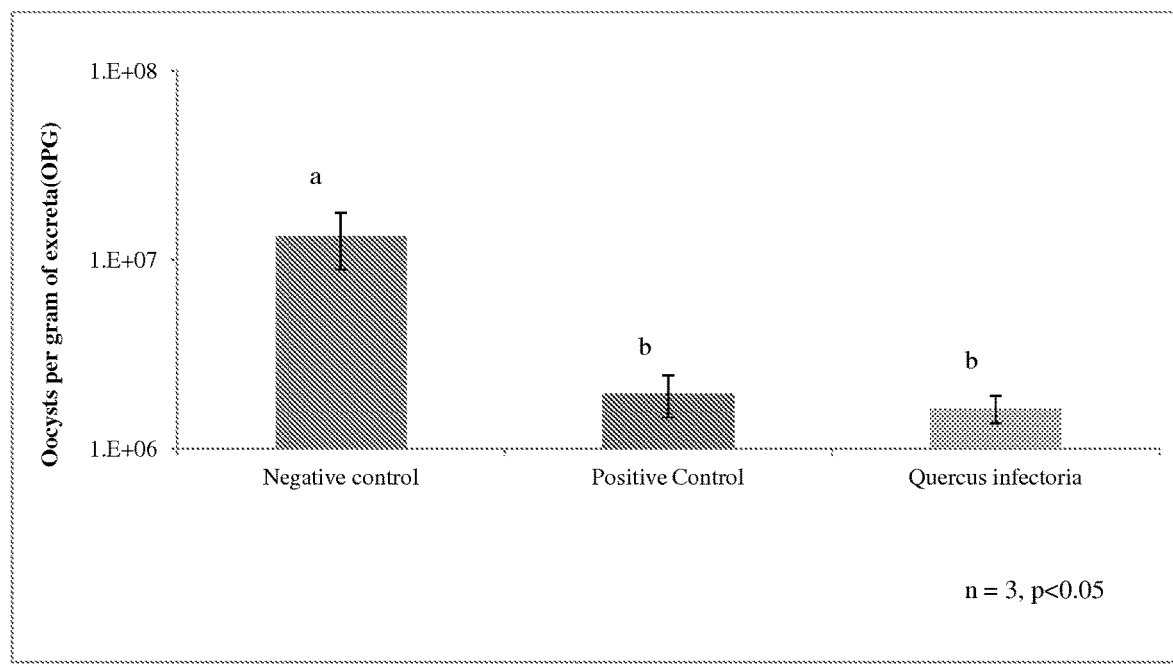
FIG. 2 is a chart of the oocysts per gram (OPG) of excreta of birds treated with *Quercus infectoria* on day 7 post infection; columns with different superscripts are statistically significant ($p<0.05$).

The OPG of excreta was estimated on day 7 post infection to evaluate the shedding of oocysts. The results of the study showed that the positive control, $Q.$ $infectoria$ had significantly lower counts of oocysts in the excreta as compared to the infected negative control ($p<0.05$). $Q.$ $infectoria$ treatment was equally effective as the positive control (FIG. 2). This correlates with the results of the lesion score.

Mortality.

The rate of mortality was recorded during the experiment, and the data are given in Table 8. As expected, there was no mortality in the uninfected control group (C1) and the positive control group (C3). $Q.$ $infectoria$ supplemented group showed no mortality.

TABLE 8

Rate of mortality during the trial period

| Treatment Groups | Rate of mortality (%) |
|---|---|
| C1 - Uninfected control | 0 |
| C2 - Negative infected control | 33.33 |
| C3 - Positive Control | 0 |
| T - Q. infectoria | 0 |

Histopathological Analysis of Caecum Samples.

$Q.$ $infectoria$ showed positive reductions in all parameters tested such as lesion score, OPG and rate of mortality and the data were comparable to the positive control, Salinomycin. Hence, histopathological analysis of the caecum samples of birds from this group was carried out in comparison to the uninfected control (C1), negative control (C2) and positive control (C3). The severity and distribution of the lesions in the caecum were based on the grading provided in Table 9.

TABLE 9

Severity and distribution of lesions in the caecum of different groups

| Histopathology | Uninfected control | Negative control | Positive control | Quercus infectoria |
|---|---|---|---|---|
| Mononuclear cell infiltration-mucosa | 0 | 3 | 2 | 1 |
| Mononuclear cell infiltration-submucosa | 0 | 2 | 3 | 0 |
| Mononuclear cell infiltration-muscular layer | 0 | 2 | 0 | 0 |
| Hemorrhages | 0 | 2 | 1 | 0 |
| Necrosis-Villi | 0 | 1 | 1 | 1 |
| Distribution of stages of Eimeria | 0 | 3 | 1 | 1 |

TABLE 10

Histopathological findings of the tissues of caecum of birds

| Groups | Histopathological findings |
|---|---|
| Uninfected control C1 | Cecum within normal histological limits. |
| Negative control C2 | Cecum showed moderate load of different Eimerial stages (oocyst, schizont and merozoite) along with mild mucosal hemorrhages and mild to moderate mononuclear cell infiltration in mucosal, submucosal and muscular layers. |
| Positive control C3 | Cecum showed minimal load of different Eimerial stages with schizonts and merozoites contributing the major load. Minimal mucosal hemorrhages and necrosis was evident microscopically. Mild to moderate mononuclear cell infiltration in mucosal and submucosal layers was seen. |
| Q. infectoria T | Cecum showed minimal load of different Eimerial stages with oocyst contributing the major load. Minimal mucosal necrosis and mononuclear cell infiltration in mucosal layers was evident. |

Figure 3:
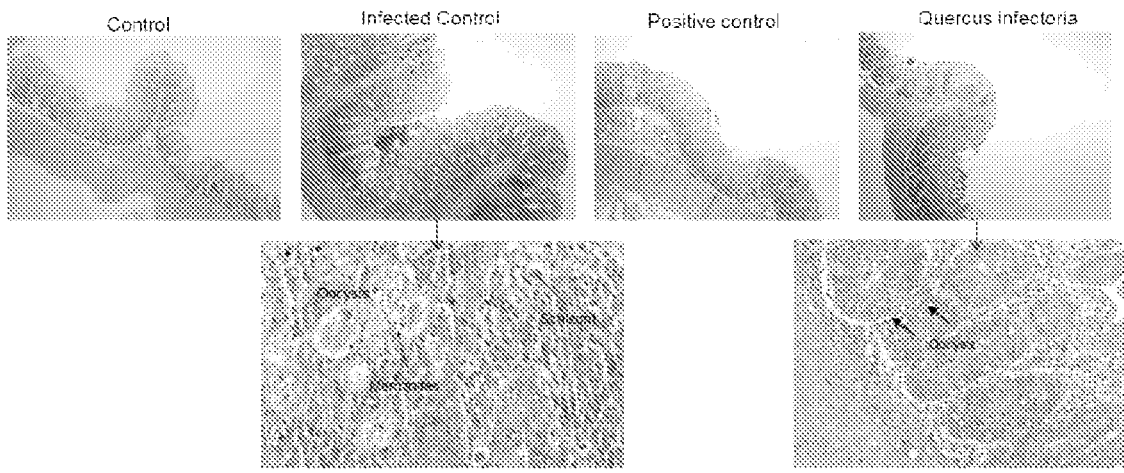
FIG. 3 is microphotographic images of the H and E stained sections of caecum of birds treated with *Quercus infectoria*.

Histopathological results showed that the birds treated with $Q.$ $infectoria$ had fewer regions of the caecum infected with $E.$ $tenella$, and the mononuclear infiltration was restricted only to the mucosa with a score of 1 indicating mild infiltration (FIG. 3). The submucosa and muscular layers were free from infiltration (Table 10). In the negative control, mononuclear infiltration was observed in the mucosa, submucosa and even the muscular layer. There were no hemorrhages in the caecum of birds treated with $Q.$ $infectoria$ as compared to that of the negative control (2). This indicates that the caecum of birds treated with $Q.$ $infectoria$ was less infected than the positive control.

The in vivo screening of plant extracts revealed that $Quercus$ $infectoria$ is a potent candidate in controlling caecal coccidiosis in broiler birds caused by $E.$ $tenella$. The efficacy of the extract was found to be on par with that of the positive control in terms of reducing lesion score, OPG and rate of mortality.

Example 3—Efficacy of Water Extracts of *Quercus Infectoria* in Controlling Mixed Infection of Coccidiosis Efficacy of $Q.$ $infectoria$ crude powder in controlling mixed infection of coccidiosis in broiler birds was evaluated. A 35 day in vivo trial was conducted wherein the birds were challenged with field strains of mixed culture of oocysts of the species *E. tenella, E. acervulina* and *E. maxima*. The mixed culture of oocysts was provided by Department of parasitology, Tamil Nadu Veterinary Research Institute, Namakkal, India. The oocysts culture was a mixture of *E. tenella, E. acervulina* and *E. maxima* isolated from feces of birds with clinical coccidiosis infection. Virulence of the oocysts obtained was evaluated in broiler birds and the dosage of the oocysts was finalized to be $5 \times 10^5$ based on the concentration that yields a lesion score of 3 and above for all the tested oocysts, *E. tenella, E. maxima* and *E. acervulina*.

a. The screening trial was conducted at Kemin's in-house R&D poultry farm facility located in Gummidipundi, India. Straight run commercial hybrid broiler chickens, *Gallus domesticus* (Var. Vencobb 400) were used for the study. Day old male chicks were procured, weighed individually, wing banded, and randomly segregated into groups. The experimental design is detailed in Table 11. Good farm managing practices and vaccination schedule were followed during the $3^{rd}$ in vivo trial as mentioned in example 1.

TABLE 11

Study design

| Category | Trial Parameter |
|---|---|
| Duration of the trial | 35 days |
| Breed | Cobb 400 |
| Rearing type | Cages |
| Age of birds at the start of the trial | 1 day old |
| Total no of Birds | 315 |
| Number of groups | 21 |
| No of birds/groups | 15 (male) |

The birds were vaccinated for Newcastle Disease Virus (NDV) and Infectious Bursal Disease (IBD). A corn soya based mash diet was used for the study. The birds were fed with the extract of *Q. infectoria* gall nut incorporated in the feed from day 1. The treatment groups are given in Table 12.

TABLE 12

Details of treatment groups for the trial

| Groups | Diet |
|---|---|
| Control 1 | No infection + normal feed |
| Control 2 | Coccidiosis induction + normal feed without anticoccidial |
| Control 3 | Coccidiosis induction + Normal feed with Coxistac 12% premix (500 g/ton) |
| Treatment | Coccidiosis induction + Normal feed with *Q. infectoria* water extract at 100 g/ton |

Extracts of gall nut of *Q. infectoria* were prepared by mixing the crude powder (100-800 micron particle size) in distilled water at the ratio of 1:2, then extracting at 80 to 90° C. for one and half hour with agitation. The extract was filtered and again the residue was extracted in water in a similar manner. This was repeated for about 2 more times and the total liquid extract was freeze dried.

Figure 4:
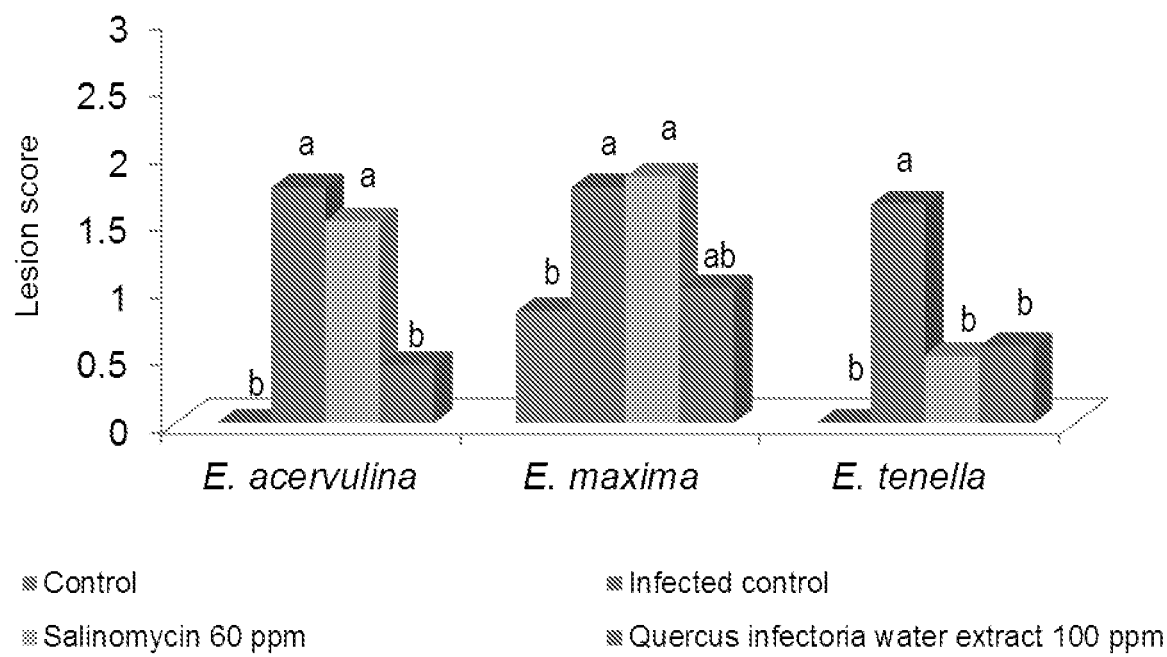
FIG. 4 is a chart of the lesion score for *E. acervulina, E. maxima* and *E. tenella* for the birds treated with *Q. infectoria* water extract on day 5 post infection; columns with different superscripts are statistically significant (p<0.05).

The results showed that there was significant reduction in the lesion score for *E. tenella* and *E. acervulina* as compared to the infected control and even the positive control, Salinomycin. Whereas, in case of *E. maxima*, a numerical reduction in the lesion score was observed as compared to the infected control and Salinomycin (FIG. 4). The oocysts per gram of treated groups were significantly lower than the infected control and Salinomycin group (FIG. 5), however, mortality was not observed in any of the treatment groups including the infected control. This proves the efficacy of *Q. infectoria* in controlling coccidiosis caused by other species of *Eimeria* also.

Example 4—In Vitro Anti-Sporozoite Activity of *Q. Infectoria* by MTT Assay

Further, an in vitro method based on 3-(4,5-Dimethyl-2-thiazolyl)-2,5-diphenyl-2H-tetrazolium bromide (MTT) reduction assay was developed to evaluate the anti-sporozoite activity of plant extracts as a measure of the viability of the sporozoites. The optimized method included the preparation, sterilization and purification of sporozoites, followed by incubation of sporozoite suspension (minimum of $10^5$ cells/ml) with required concentration of plant extract. The plant samples were prepared by mixing crude powder into a known volume of distilled water to achieve the specific ppm, vortexed for 2 min and filtered through a 0.2μ syringe filter. Following 24 h of incubation with the plant extracts, the sporozoites were thoroughly washed and then MTT assay was performed. MTT-PMS solution (0.2 millimolar each) is incubated with the sporozoite suspension (at 1:10 ratio) for 2 h at 41° C. After incubation, the contents are centrifuged at 800 g for 5 min and the supernatant is carefully removed. The purple dye formazan is dissolved in 200 ul DMSO and the absorbance is measured at 530 nm against a reference wavelength of 630 nm.

MTT assay was carried out for the evaluation of *Q. infectoria* at various dosage levels along with Coccidiostac (Salinomycin) as positive control (FIG. 6). There was a dose dependent reduction in the viability of sporozoites in the *Q. infectoria* treated samples as compared to the control.

Example 5—In Vitro Effect of *Q. Infectoria* on *Eimeria Tenella* Sporozoite Invasion and Proliferation in Host Cells An experiment was conducted to evaluate the in vitro effect of *Q. infectoria* on *Eimeria tenella* sporozoite invasion and proliferation of host cells.

Sporozoites were obtained from sporulated oocysts after glass bead grinding and enzymatic excystation. As host cells, Madin-Darby Bovine Kidney (MDBK) cells, were selected. Sporozoites and *Quercus infectoria* at 50 and 100 ppm were added to MDBK host cells for four hours. Afterwards, the medium was removed, cells were washed and fresh medium was added. After 4 (T4), 24 (T24), 48 (T48) and 72 (T72) hours the medium and MDBK cells were collected and stored at −20° C.

The negative control (neg ctrl) was MDBK cells infected with *Eimeria* sporozoites, incubated in cell culture medium. The positive control (pos ctrl) was MDBK cells infected with *Eimeria* sporozoites, incubated with a 5 μg/ml solution of Salinomycin.

Figure 7:
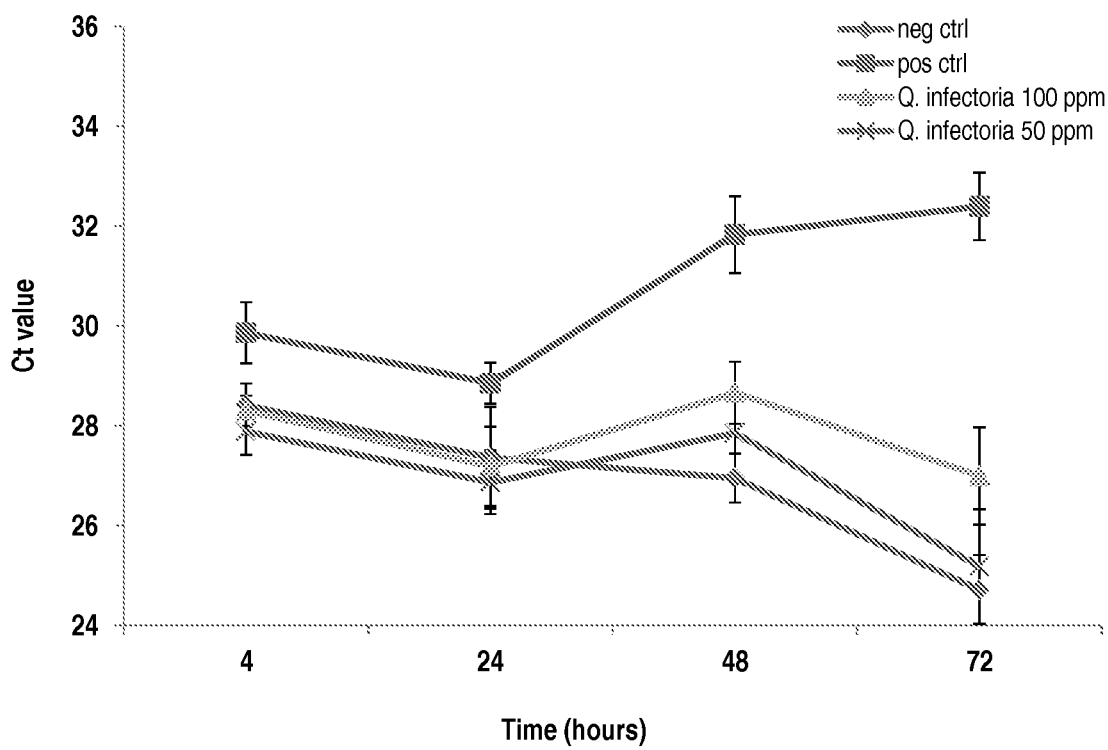
FIG. 7 is a chart of PCR results after invasion of MDBK host cells with sporozoites and different concentrations of *Q. infectoria*.

At the different collection time points, DNA was extracted from the infected MDBK cells. Real-time PCR to detect *Eimeria* DNA was performed on the samples for the different time points and different treatments. The PCR results are presented in FIG. 7.

Real-Time PCR Analyses

Differences in Ct values were calculated for each time point versus T4 within one treatment (ΔCt). Fold changes were calculated for each time point versus T4 using the following equation:

Fold change=$2^{-\Delta Ct}$

Figure 8:
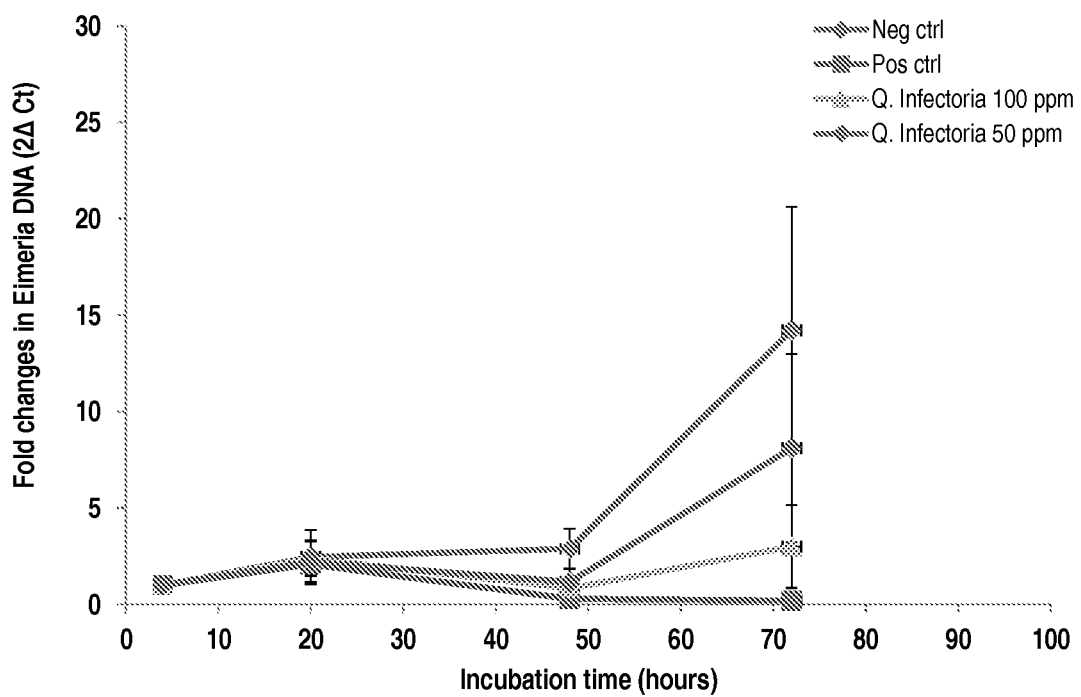
FIG. 8 is a chart of fold changes in *Eimeria* DNA for different time points versus T4 within one treatment.

These results are presented in FIG. 8.

The negative control shows a clear *Eimeria* proliferation since there is a 15 fold increase in *Eimeria* DNA at 72 hours versus the start at 4 hours. The positive control was able to inhibit the proliferation completely. Also for the *Q. infectoria* treatments, a clear inhibition of the proliferation was observed versus the start of 4 hours, in a dose dependent manner.

Example 6—In Vitro Effect of *Q. Infectoria* on *Eimeria Tenella* Sporozoite Invasion and Proliferation in Host Cells An experiment was conducted to evaluate the in vitro effect of *Q. infectoria* on *Eimeria tenella* sporozoite invasion and proliferation in host cells.

Sporozoites were obtained from sporulated oocysts after glass bead grinding and enzymatic excystation. As host cells, Madin-Darby Bovine Kidney (MDBK) cells, were selected. Sporozoites were pre-treated with 50, 100 and 250 ppm of *Quercus infectoria* for three hours. Thereafter, the sporozoite suspension was washed and put onto a culture of MDBK cells for 20 hours. After incubation, the medium was removed, cells were washed and fresh medium was added. After 20, 72 and 96 hours the medium and MDBK cells were collected and stored at −20° C.

The negative control (neg ctrl) was MDBK cells infected with *Eimeria* sporozoites, incubated in cell culture medium. The positive control (pos ctrl) was MDBK cells infected with *Eimeria* sporozoites, incubated with a 5 µg/ml solution of Salinomycin.

Figure 9:
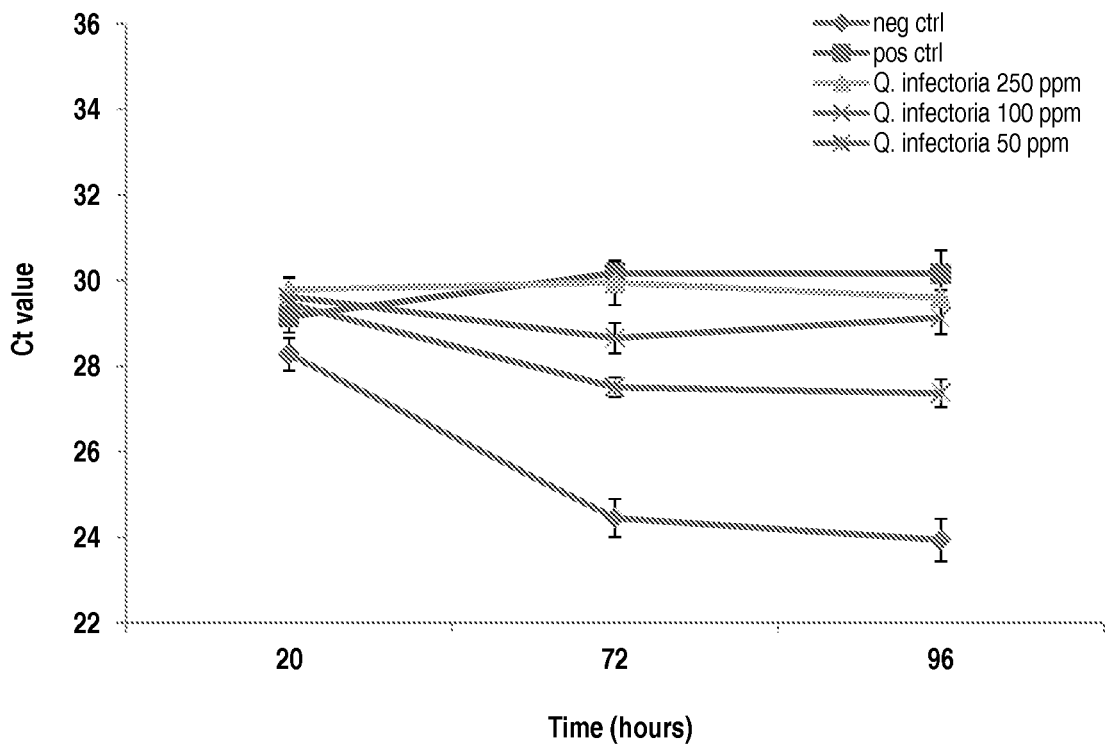
FIG. 9 is a chart of PCR results after invasion of MDBK host cells with sporozoites, pre-treated with different concentrations of *Q. infectoria*.

At the different collection time points, DNA was extracted from the MDBK cells. Real-time PCR to detect *Eimeria tenella* DNA was performed on the samples for the different time points and different treatments. The PCR results are presented in FIG. 9.

Real-Time PCR Analyses

Differences in Ct values were calculated for each time point versus T20 within one treatment (ΔCt). Fold changes were calculated for each time point versus T20 using the following equation:

Fold change=$2^{-\Delta Ct}$

Figure 10:
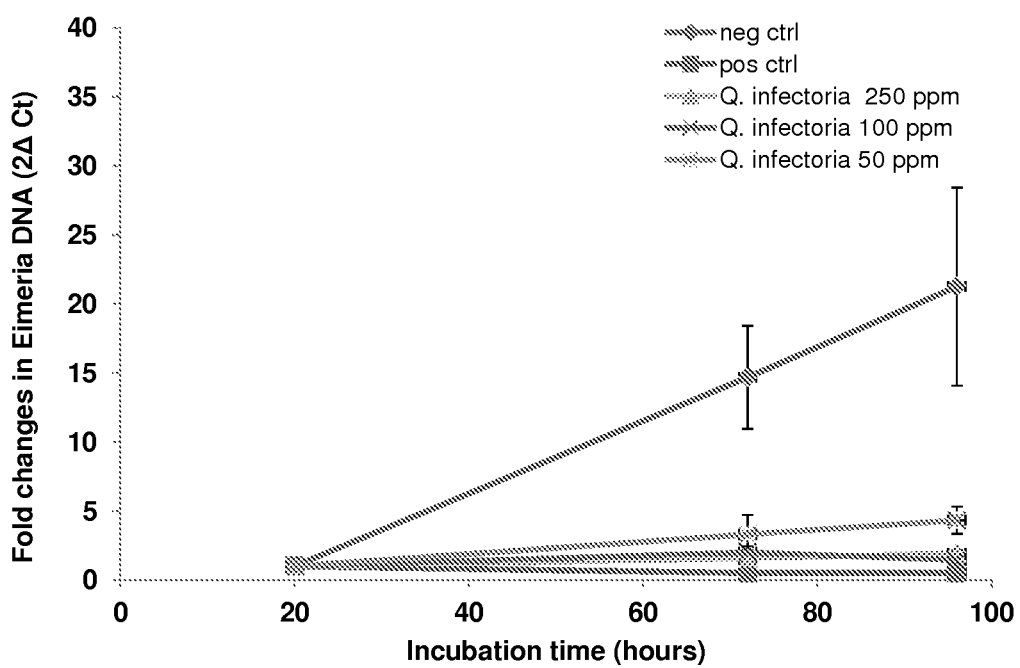
FIG. 10 is a chart of fold changes in *Eimeria* DNA for different time points versus T20 within one treatment.

These results for *Q. infectoria* are presented in FIG. 10.

The negative control shows a clear *Eimeria* proliferation since there is a 20 fold increase in *Eimeria* DNA at 96 hours versus the start at 20 hours. The positive control was able to inhibit the proliferation completely. Also the different dosages of *Q. infectoria* all inhibited the *Eimeria* proliferation. There was a slightly lower effect visible for 50 ppm *Q. infectoria*. But this is negligible in comparison to the increase in the negative control.

Example 7—Identification of Active Ingredient/s of *Q. Infectoria*

Figure 11:
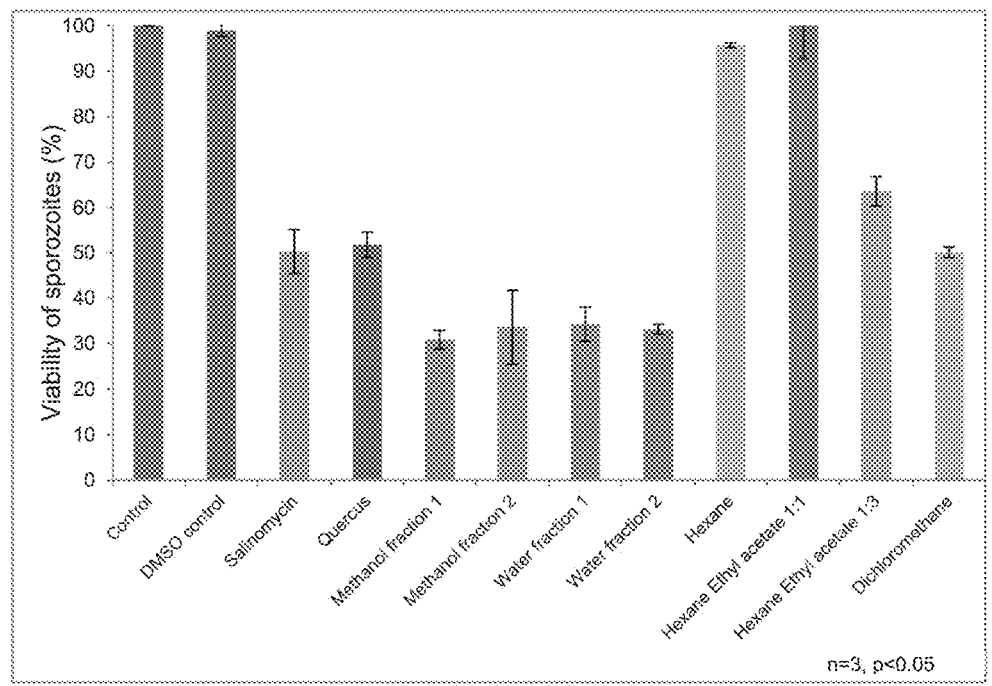
FIG. 11 is a chart of the anti-sporozoite activity of the different fractions of *Q. infectoria*; columns with different superscripts are statistically significant (p<0.05).

Further to this, Bioassay Guided Fractionation assay (BGFA) of *Q. infectoria* gall nuts was carried out using the modified MTT reduction assay as the bioassay as we had identified that the crude extract possess anti-sporozoite activity and this could be one of the mode of action by which it is able to control coccidiosis. *Q. infectoria* gall nut crude powder was fractionated using different solvent by column chromatography. The sample from each of the fractions was evaluated for their anti-sporozoite activity. Methanol and water fractions of *Q. infectoria* showed better reduction in the viability of sporozoites as compared to the other fractions and were comparable to the Salinomycin control (FIG. 11).

Figure 12:
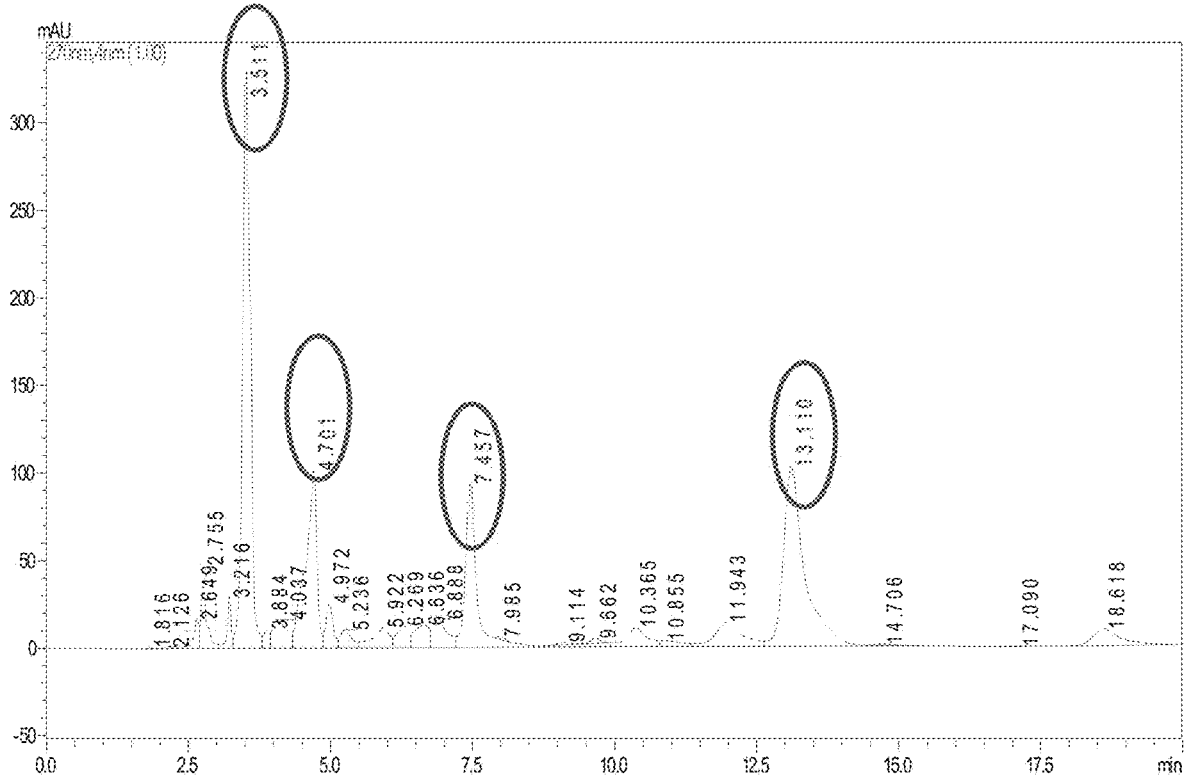
FIG. 12 is a High Performance Liquid Chromatogram (HPLC) chromatogram of water fraction of *Q. infectoria*.

Phytochemical analyses of the active fractions were carried out by High Performance Liquid Chromatography (HPLC) to identify the active ingredient/s responsible for the anti-sporozoite activity. Four major peaks were observed in the HPLC chromatogram of both methanol and water fractions, with one peak corresponding to the retention time of a gallic acid standard (FIG. 12). *Q. infectoria* gall nut are known to possess 60 to 70% hydrolysable tannins which can hydrolyse to release gallic acid in addition to about 7% free gallic acid present in it.

Figure 13:
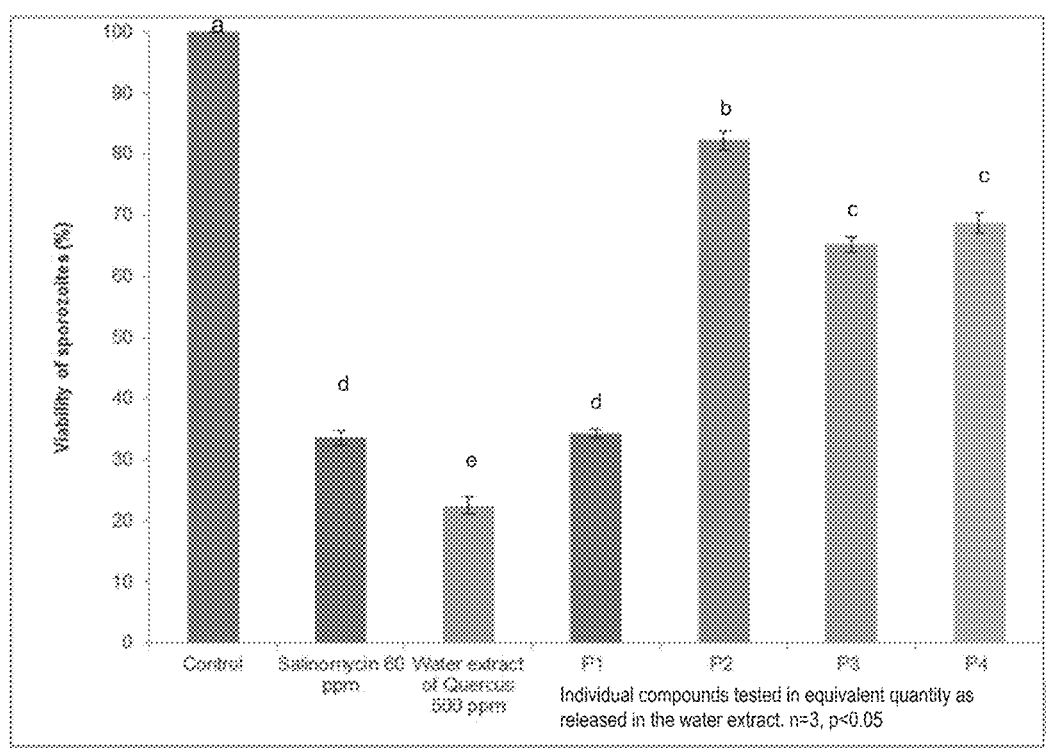
FIG. 13 is a chart of the anti-sporozoite activity of the four major peaks of *Q. infectoria*; columns with different superscripts are statistically significant (p<0.05).

These four compounds were separated by semi-preparative HPLC and anti-sporozoite activity was evaluated in comparison to the crude powder in equivalent concentrations. The anti-sporozoite activity of the compounds showed that compound of peak 1 had the best anti-sporozoite activity. The other compounds showed minimal activity against the sporozoites. However, the crude powder showed better activity than the peak 1 indicating synergistic activity of the compounds from the extract (FIG. 13).

Figure 14:
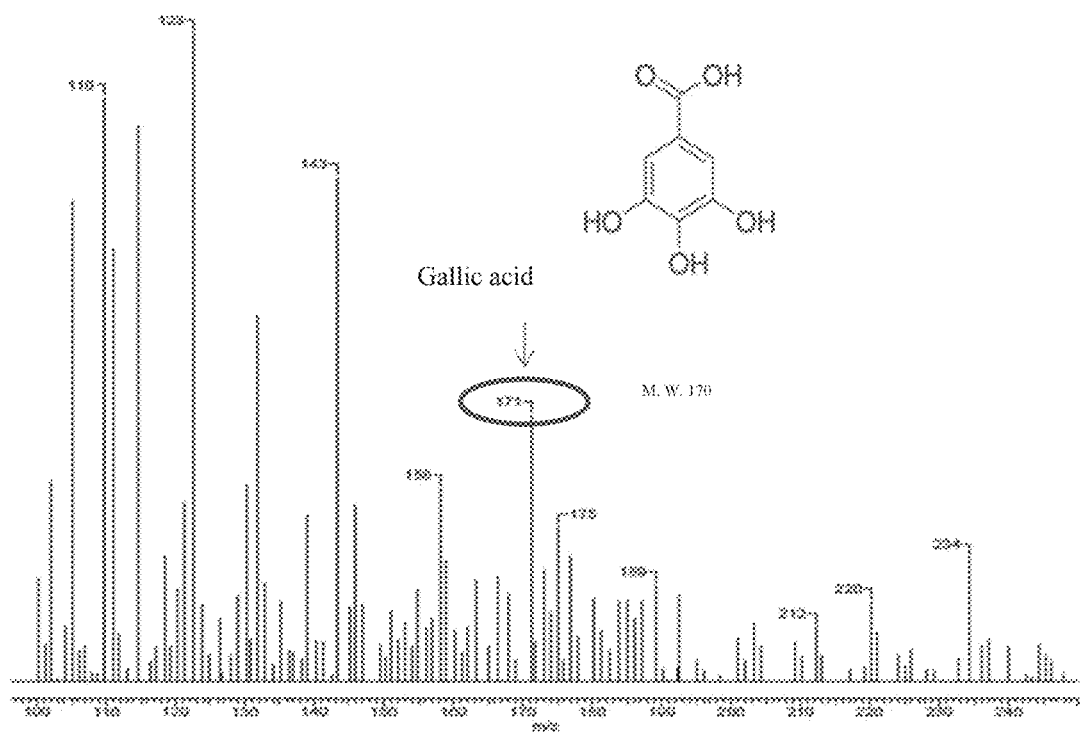
FIG. 14 is the LC/MS/MS chromatogram of peak 1 of *Q. infectoria*.

LC/MS/MS analysis of the different peaks of the HPLC chromatogram confirmed that peak 1 was gallic acid (FIG. 14) and the other peaks were high molecular weight compounds which could be degraded products of hydrolysable tannins. It was hypothesized that these compounds can further breakdown to release gallic acid.

Figure 15:
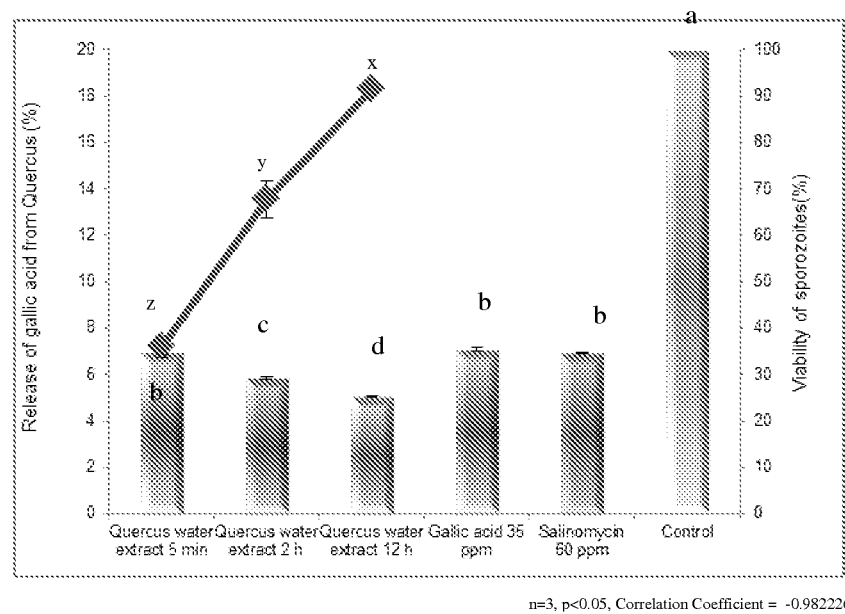
FIG. 15 is a chart depicting the correlation between the concentration of gallic acid and the anti-sporozoite activity of *Q. infectoria*; columns with different superscripts are statistically significant (p<0.05).

Further, to arrive at the correlation between gallic acid % and anti-sporozoite activity, *Q. infectoria* was extracted in water for 5 min, 2 and 12 h and their anti-sporozoite activity was evaluated. The study showed that there was a clear correlation (correlation coefficient=−0.982226) between the concentration of gallic acid and anti-sporozoite activity (FIG. 15). These results indicate that gallic acid is the active ingredient responsible for the anti-sporozoite activity of *Q. infectoria*.

Example 8—In Vitro Protective Effect of Gallic Acid

An experiment was conducted to evaluate the in vitro protective effect of gallic acid monohydrate on host cells challenged with *Eimeria tenella* sporozoites.

Sporozoites were obtained from sporulated oocysts after glass bead grinding and enzymatic excystation. As host cells, Madin-Darby Bovine Kidney (MDBK) cells, were selected. MDBK cells were incubated with 10 ppm gallic acid for seven hours. Afterwards the medium was removed and a sporozoite suspension was added to the MDBK cells for 20 hours. After incubation, the medium was removed, cells were washed and fresh medium was added. After 20, 72 and 96 hours the medium and the MDBK cells were collected and stored at −20° C.

The negative control (neg ctrl) was MDBK cells infected with *Eimeria* sporozoites, incubated in cell culture medium. The positive control (pos ctrl) was MDBK cells infected with *Eimeria* sporozoites, incubated with a 5 µg/ml solution of Salinomycin.

Figure 16:
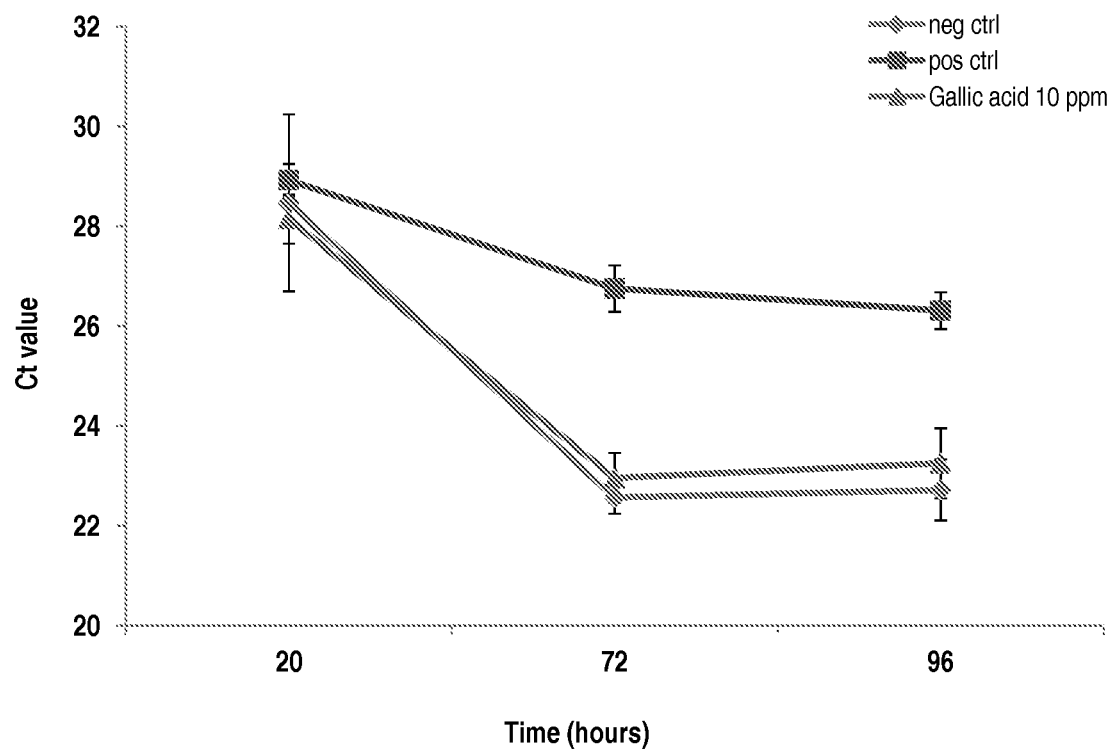
FIG. 16 is a chart of PCR results of MDBK host cells, pre-treated with 10 ppm gallic acid, invaded with sporozoites.

At the different collection time points, DNA was extracted from the MDBK cells. Real-time PCR to detect *Eimeria* DNA was performed on the samples for the different time points and different treatments. The PCR results are presented in FIG. 16.

Real-Time PCR Analyses

Differences in Ct values were calculated for each time point versus T20 within one treatment (ΔCt). Fold changes were calculated for each time point versus T20 using the following equation:

$$\text{Fold change} = 2^{-\Delta Ct}$$

Figure 17:
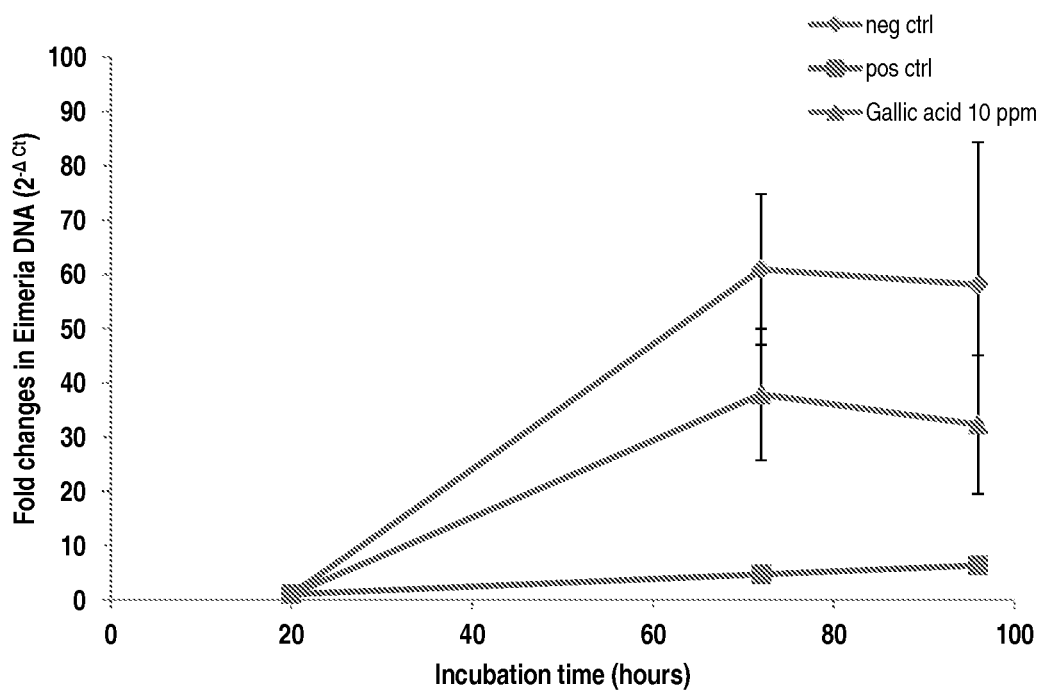
FIG. 17 is a chart of fold changes in *Eimeria* DNA for different time points versus T20 within one treatment.

These results are presented in FIG. 17.

The negative control shows a clear *Eimeria* proliferation since there is a 60 fold increase in *Eimeria* DNA at 96 hours versus the start at 20 hours. The positive control was able to inhibit the proliferation almost completely. Also for 10 ppm gallic acid treatment, a clear inhibition of the proliferation was observed in a dose dependent manner. This indicates that gallic acid at a low dose of 10 ppm is able to protect the host cells to some extend against *Eimeria* proliferation.

Example 9—In Vitro Effect of Gallic Acid on *Eimeria Tenella* Sporozoite Invasion and Proliferation in Host Cells An experiment was conducted to evaluate the in vitro effect of gallic acid monohydrate on *Eimeria tenella* sporozoite invasion and proliferation in host cells.

Sporozoites were obtained from sporulated oocysts after glass bead grinding and enzymatic excystation. As host cells, Madin-Darby Bovine Kidney (MDBK) cells, were selected. Sporozoites were pre-treated with 10, 25 and 50 ppm gallic acid monohydrate for three hours. Thereafter, the sporozoite suspension was washed and put onto a culture of MDBK cells for 20 hours. After incubation, the medium was removed, cells were washed and fresh medium was added. After 20, 72 and 96 hours the medium and MDBK cells were collected and stored at −20° C.

The negative control (neg ctrl) was MDBK cells infected with *Eimeria* sporozoites, incubated in cell culture medium. The positive control (pos ctrl) was MDBK cells infected with *Eimeria* sporozoites, incubated with a 5 µg/ml solution of Salinomycin.

Figure 18:
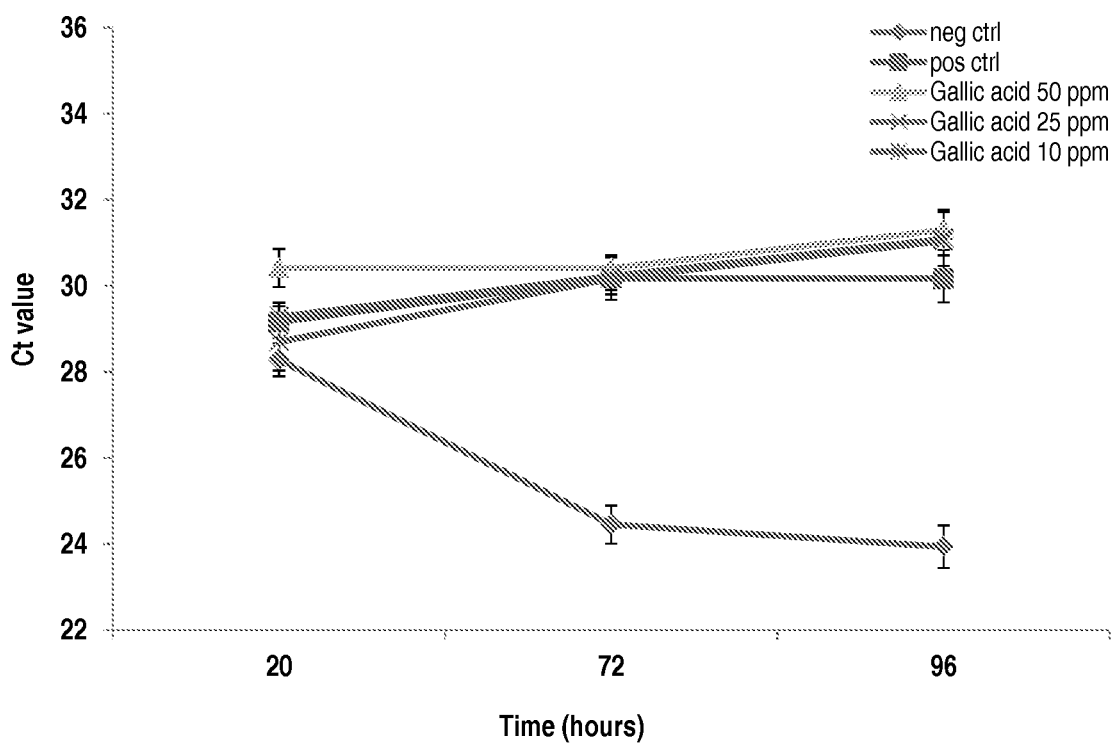
FIG. 18 is a chart of PCR results after invasion of MDBK host cells with sporozoites, pre-treated with different concentrations of gallic acid.

At the different collection time points, DNA was extracted from the MDBK cells. Real-time PCR to detect *Eimeria* DNA was performed on the samples for the different time points and different treatments. The PCR results are presented in FIG. 18.

Real-Time PCR Analyses

Differences in Ct values were calculated for each time point versus T20 within one treatment (ΔCt). Fold changes were calculated for each time point versus T20 using the following equation:

$$\text{Fold change} = 2^{-\Delta Ct}$$

Figure 19:
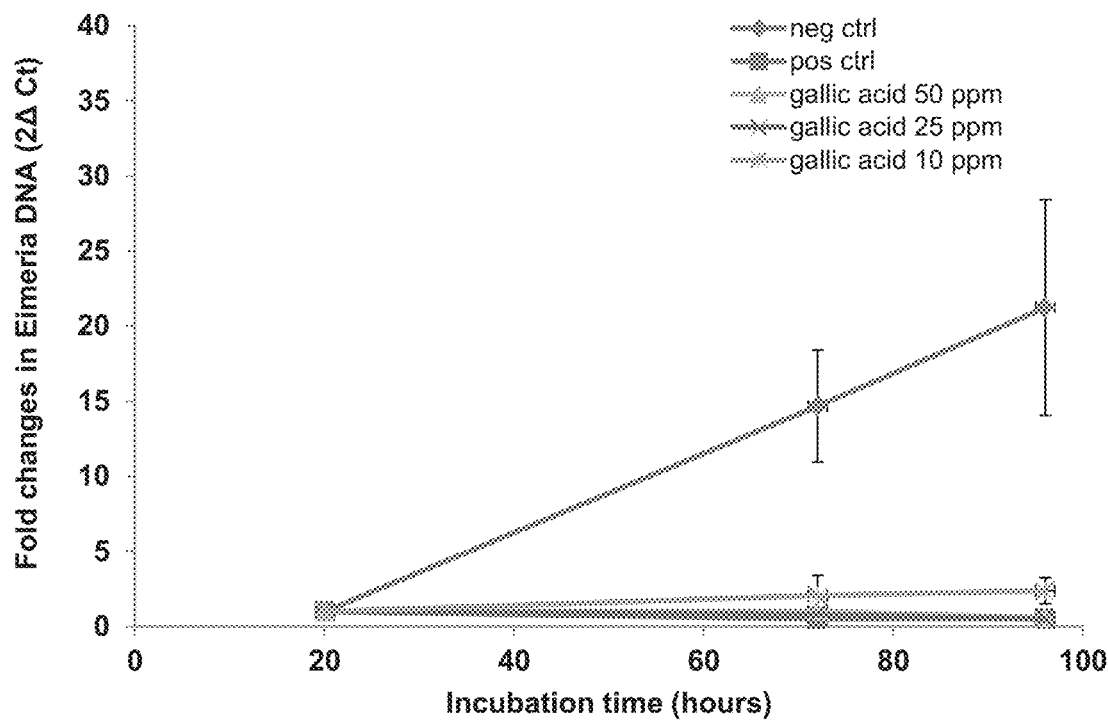
FIG. 19 is a chart of fold changes in *Eimeria* DNA for different time points versus T20 within one treatment.

These results are presented in FIG. 19.

The negative control shows a clear *Eimeria* proliferation since there is a 20 fold increase in *Eimeria* DNA at 96 hours versus the start at 20 hours. The positive control as well as the different dosages of gallic acid inhibited the *Eimeria* proliferation. There was a slightly lower effect visible for 10 ppm gallic acid. But this is negligible in comparison to the increase in the negative control.

Example 10—Efficacy of Gallic Acid in Controlling Coccidiosis

Figure 20:
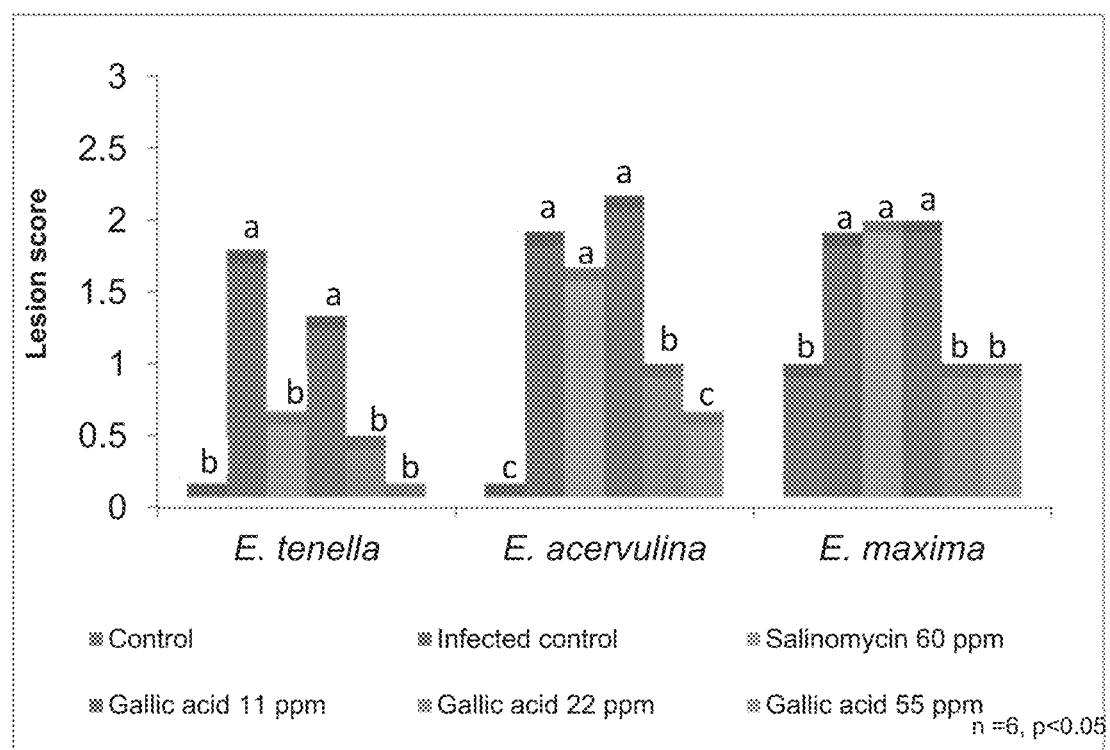
FIG. 20 is a chart of the lesion score on day 5 post infection of birds treated with gallic acid at different concentrations; columns with different superscripts are statistically significant (p<0.05).
Figure 21:
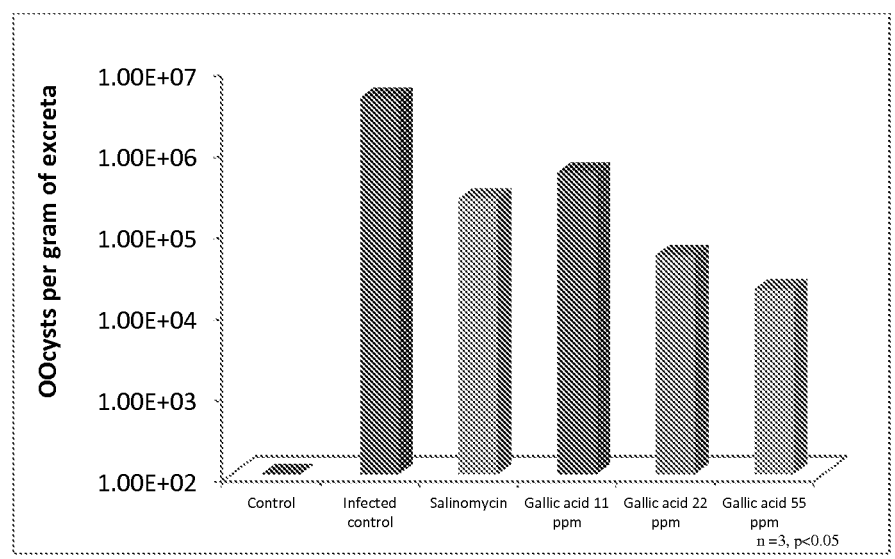
FIG. 21 is a chart of the OPG on day 7 post infection of birds treated with gallic acid at different concentrations; columns with different superscripts are statistically significant (p<0.05).

The efficacy of gallic acid at three different dosages of 11, 22 and 55 ppm in controlling coccidiosis in broiler birds was evaluated by an in vivo challenge trial. The birds were induced with mixed infection of *Eimeria* using oocysts of *E. tenella*, *E. maxima* and *E. acervulina*. These oocysts were isolated from birds confirmed with clinical coccidiosis. The trial design, oocysts dosage, vaccination schedule, farm maintenance were similar to that of example 3. The lesion scoring showed that there was significant reduction in the score for all the three tested species of *Eimeria* as compared to the infected control and even the positive control, Salinomycin (FIG. 20). The oocysts per gram showed a similar trend (FIG. 21), however, mortality was not observed in any of the treatment groups including the infected control. Dose dependent response was observed with no significant difference between gallic acid at 22 and 55 ppm. This shows that gallic acid is able to control mixed infection of coccidiosis in broiler birds. It is also evident that gallic acid is the active ingredient responsible for the anticoccidial activity of *Q. infectoria*.

Example 11—Anti-Sporozoite Activity of Plants Containing Gallic Acid

Further, other plants that contain gallic acid were also evaluated for their anti-sporozoite activity and anticoccidial activity in broiler birds. The plants chosen were *Rhus chinensis* (Chinese gall nut) and *Terminalia chebula* (Indian gall nut). *Rhus chinensis* contains about 70% hydrolysable tannins and *Terminalia chebula* contains around 0.28% free gallic acid. However, *T. chebula* contains 25 to 40% hydrolysable tannins which can degrade to release gallic acid. These plants have been reported for their antioxidant, antiinflammatory, antibacterial, antifungal, antimutagenic and anticancer activities.

Figure 22:
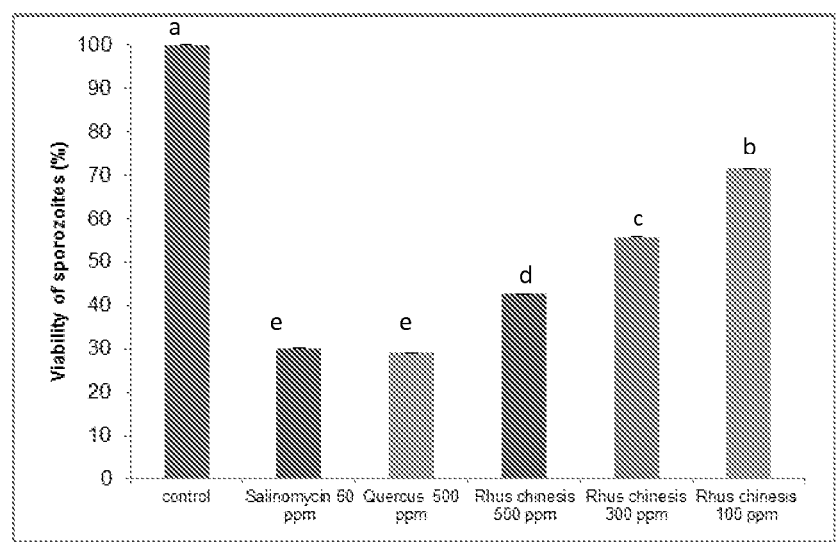
FIG. 22 is a chart of the anti-sporozoite activity of *Rhus chinensis* and *Terminalia chebula*; columns with different superscripts are statistically significant (p<0.05).

Crude powder of fruit of *Terminalia chebula* and gall nut of *Rhus chinensis* were obtained from Natural Remedies, Bangalore, India and Xinjiang, China respectively. The anti-sporozoite assay by MTT assay showed that both the tested plants were able to reduce the viability of sporozoites as compared to the control and better than the positive control, Salinomycin (FIG. 22).

Example 12—In Vitro Effect of Plants Containing Gallic Acid on *Eimeria Tenella* Sporozoite Invasion and Proliferation in Host Cells An experiment was conducted to evaluate the in vitro effect of other sources of gallic acid on *Eimeria tenella* sporozoite invasion and proliferation in host cells.

Sporozoites were obtained from sporulated oocysts after glass bead grinding and enzymatic excystation. As host cells, Madin-Darby Bovine Kidney (MDBK) cells, were selected. Sporozoites were pre-treated with 50, 100 and 250 ppm of *Terminalia chebula* for three hours. Thereafter, the sporozoite suspension was washed and put onto a culture of MDBK cells for 20 hours. After incubation, the medium was removed, cells were washed and fresh medium was added. After 20, 72 and 96 hours the medium and MDBK cells were collected and stored at −20° C.

The negative control (neg ctrl) was MDBK cells infected with *Eimeria* sporozoites, incubated in cell culture medium. The positive control (pos ctrl) was MDBK cells infected with *Eimeria* sporozoites, incubated with a 5 µg/ml solution of Salinomycin.

Figure 23:
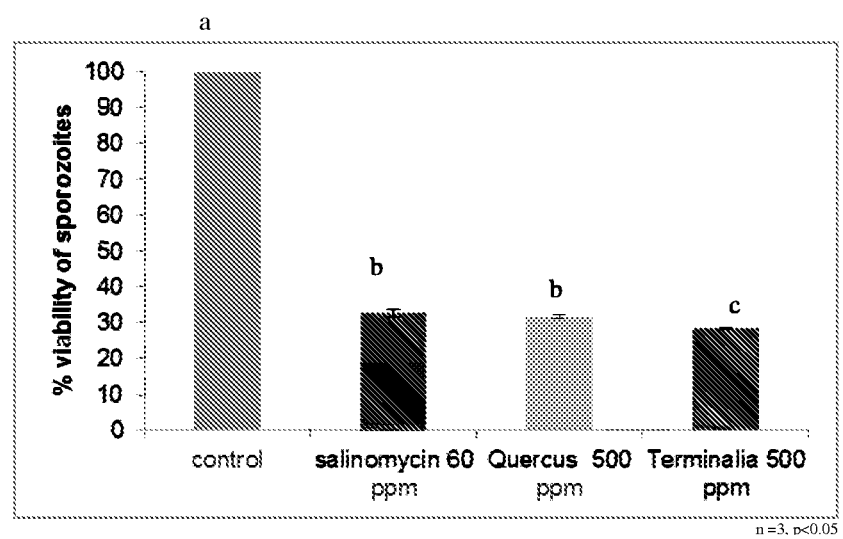
FIG. 23 is a chart of PCR results after invasion of MDBK host cells with sporozoites, pre-treated with different concentrations of *T. chebula*.

At the different collection time points, DNA was extracted from the MDBK cells. Real-time PCR to detect *Eimeria tenella* DNA was performed on the samples for the different time points and different treatments. The PCR results are presented in FIG. 23.

Real-Time PCR Analyses

Differences in Ct values were calculated for each time point versus T20 within one treatment (ΔCt). Fold changes were calculated for each time point versus T20 using the following equation:

Fold change=$2^{\Delta Ct}$

Figure 24:
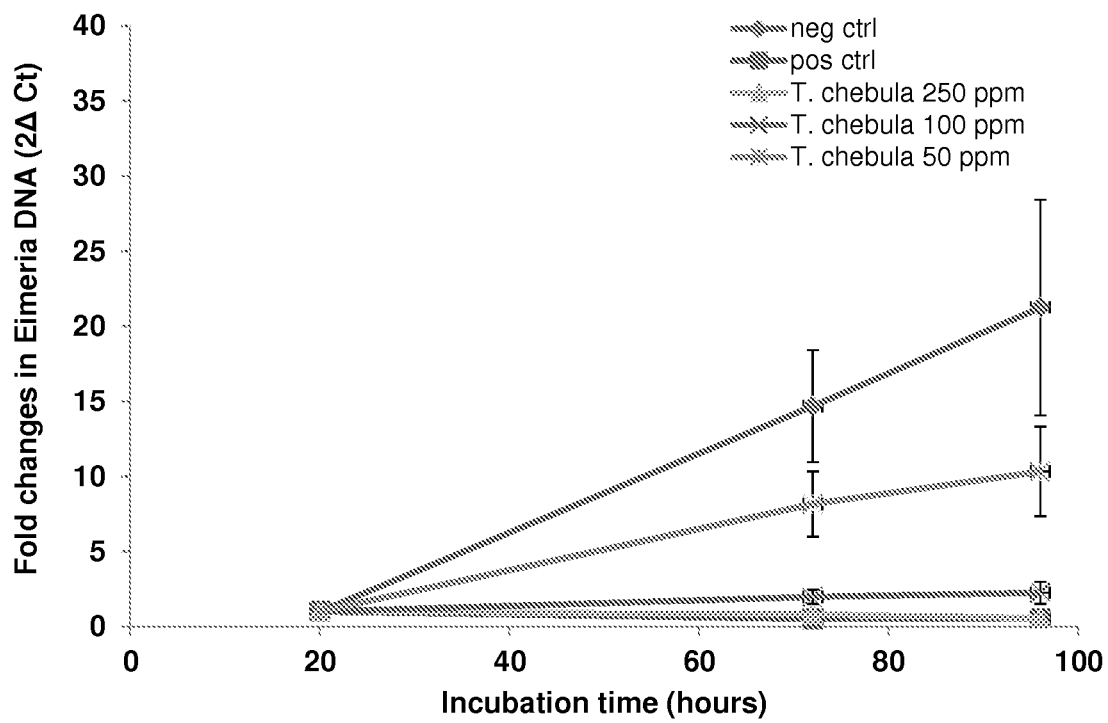
FIG. 24 is a chart of fold changes in *Eimeria* DNA for different time points versus T20 within one treatment.

These results for *T. chebula* are presented in FIG. 24.

Figure 25:
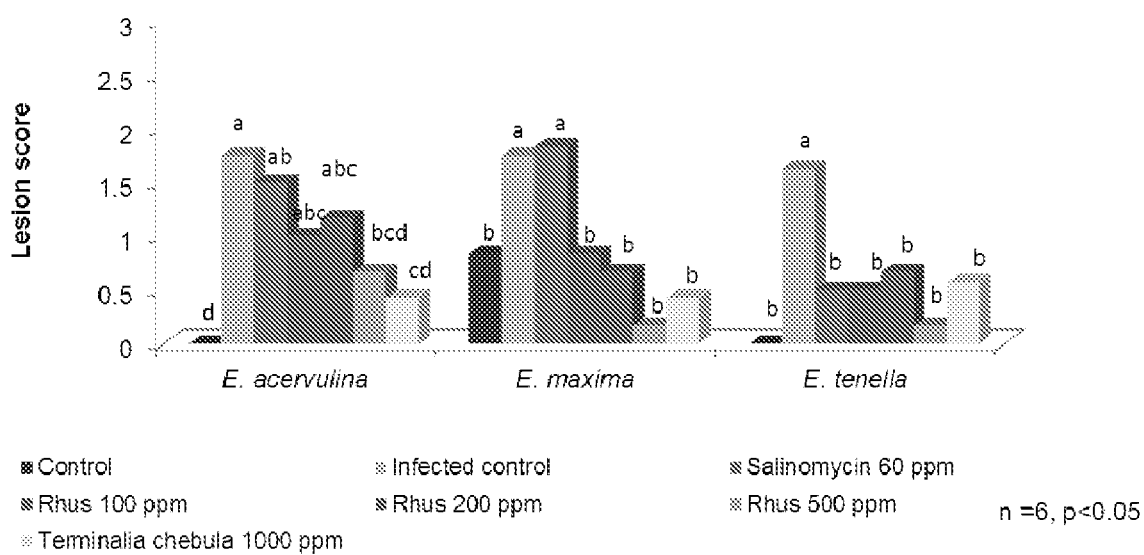
FIG. 25 is a chart of the lesion score on day 5 post infection of birds treated with *R. chinensis* and *T. chebula*; columns with different superscripts are statistically significant (p<0.05).
Figure 26:
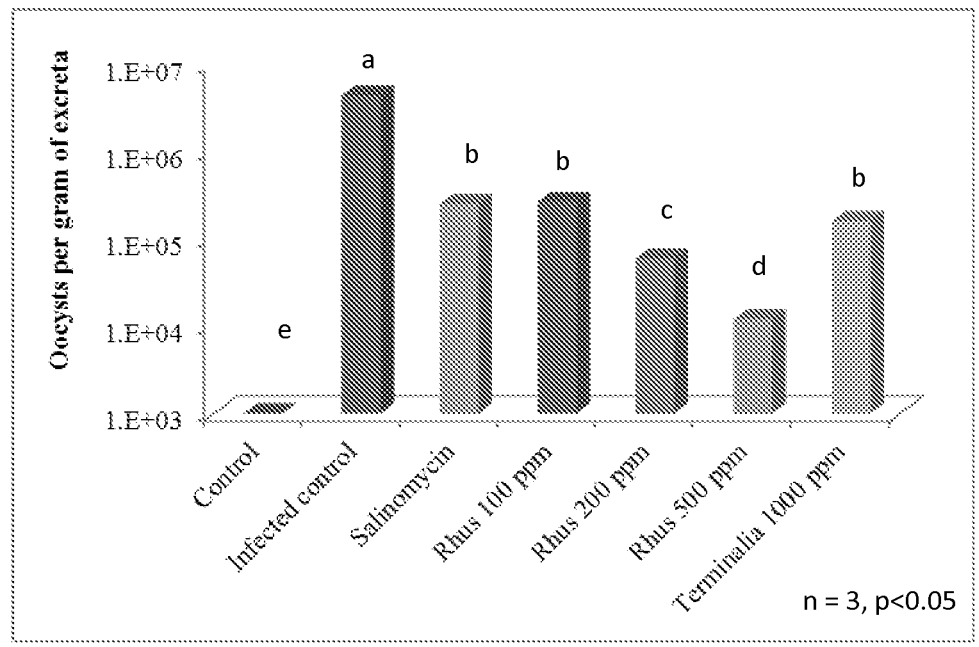
FIG. 26 is a chart of the OPG on day 7 post infection of birds treated with *R. chinensis* and *T. chebula*; columns with different superscripts are statistically significant (p<0.05).

The negative control shows a clear *Eimeria* proliferation since there is a 20 fold increase in *Eimeria* DNA at 96 hours versus the start at 20 hours. The positive control as well as 250 ppm *T. chebula* completely inhibited the *Eimeria* proliferation. There was a dose-response effect visible although the lower effect for 100 ppm *T. chebula* is negligible in comparison to the increase in the negative control Example 13—Efficacy of Plants Containing Gallic Acid in Controlling Coccidiosis The efficacy of plants containing gallic acid namely, *Terminalia chebula* and *Rhus chinensis* in controlling coccidiosis in broiler birds was evaluated by an in vivo challenge trial. The birds were induced with mixed infection of *Eimeria* using oocysts of *E. tenella, E. maxima* and *E. acervulina* isolated from birds confirmed with clinical coccidiosis. The trial design, oocysts dosage, vaccination schedule, farm maintenance were similar to that of example 3. The lesion scoring showed that *Rhus chinensis* at 200 and 500 ppm and *Terminalia chebula* at 1000 ppm were able to reduce the score for all the three tested species of *Eimeria* as compared to the infected control and even the positive control, Salinomycin (FIG. 25). The oocysts per gram showed a similar trend (FIG. 26), however, mortality was not observed in any of the treatment groups including the infected control. Dose dependent response was observed with *Rhus chinensis*.

Example 14—Efficacy of Encapsulated and Microemulsion Forms of 3,4,5-Trihydroxybenzoicacid (Thb) in Controlling Coccidiosis in Broiler Birds An in vivo trial was conducted in commercial broiler, Cobb 400 to evaluate the efficacy of encapsulated and microemulsion forms of 3,4,5-trihydroxybenzoic acid (THB) in controlling coccidiosis caused by *E. maxima*. The trial was designed with 11 treatment groups with 2 replicates per groups and 12 male birds per replicate. The groups included (1) uninfected control, (2) infected control, (3) positive control groups supplemented with Salinomycin (Coxistac) at the recommended dosage, (4) treatment group treated with 20 and 50 g/ton of pure THB, (5) encapsulated THB at 46.3, 92.6 and 185.2 g/ton of feed, and (6) microemulsion of THB at 138.9, 277.8 and 416.7 g/ton of feed. Coccidiosis was experimentally induced by orally challenging the birds with sporulated oocysts of *Eimeria maxima* at a dose of $2 \times 10^4$ oocysts/bird/day on day 14, 15 and 16 day of age. The parameters evaluated were lesion scoring on day 6 post challenge and oocysts shedding on day 7 post-challenge. The results of lesion scoring showed that pure THB at 50 and 75 ppm showed comparable efficacy. The encapsulated THB treated birds showed a dose response trend with 12.5 ppm comparable to pure THB at 25 ppm. Supplementation of encapsulated THB at 50 ppm reduced the lesions to nil and was significantly (P<0.01) better than all the other groups. No dose response effect was observed with the microemulsion of THB. Supplementation of microemulsion of THB at 12.5 ppm was comparable to 25 and 50 ppm of pure THB. The oocysts shedding in the excreta indicated that the infected controls had highest oocysts shedding. All other treatment groups showed significant reduction in the oocysts shedding as compared to the infected control (p<0.01). Encapsulated and microemulsion of THB showed better efficacy at lower dosage as compared to the pure THB.

We have previously discovered that supplementation of 3,4,5-trihydroxybenzoicacid (THB)/gallic acid was able to control coccidiosis caused by *Eimeria acervulina, E. maxima* and *E. tenella* in broilers. The aim of the present study was to evaluate the efficacy of microemulsion and encapsulated forms of THB in controlling coccidiosis. *E. acervulina, E. maxima* and *E. tenella* are the most prevalent out of the seven species of *Eimeria* that cause infection in poultry (Rao, V. P., Raman, M., Raj, D. G., Basith, A. S and Gomathinayagam. S. (2012). Speciation of poultry *eimeria* by morphology and SCAR PCR in Southern India. Indian J. Ani. Sci., 82(8): 805-811). Among these, *E. maxima* is considered to be the one with the highest pathogenicity (Sharman, P. A., Smith, N. C., Wallach, M. G and Katrib, M. (2010). Chasing the golden egg: vaccination against poultry coccidiosis. Parasite Immunol., 32(8): 590-598), causing lesions that may compromise the absorption surface of birds' digestive tract (Jang, S. I., Lillehoj, H. S., Lee, S. H., Lee, K. W., Park, M. S and Cha, S. R. (2010). *Eimeria maxima* recombinant Gam82 gametocyte antigen vaccine protects against coccidiosis and augments humoral and cell-mediated immunity. Vaccine. 28(17): 2980-2985). In addition, it may also favor establishment of other diseases, since the damaged intestinal tissues and the functional changes to the intestinal tract that it causes may break down the natural defense barriers and allow colonization by various pathogenic agents (Freitas, F. L. C (2014). Metabolic alterations in broiler chickens experimentally infected with sporulated oocysts of *Eimeria maxima*. Braz. J. Vet. Parasitol., 23 (3), 309-314). *E. maxima* has affinity for lateral and apical areas of the villi, causing destruction of the villi with consequent decreased capacity for intestinal digestion and absorption of nutrients such as zinc, oleic acid, methionine, histidine, calcium, glucose and xanthophyll (Lillehoj, H. S and Okamura, M. (2003). Host immunity and vaccine development to coccidia and salmonella infections in chickens. Poult. Sci., 40(3): 151-193), thus altering the biochemical and hematological parameters. Considering the importance of intestinal villus integrity for nutrient absorption and performance in poultry, the objective of the present study was to evaluate the efficacy of microemulsion and encapsulated THB in controlling coccidiosis caused by *E. maxima*.

Materials and Methods

Microemulsion of THB.

The samples of microemulsified THB were prepared using THB monohydrate (90% purity, Sigma Aldrich). Briefly, the THB microemulsion was prepared by using the bio-continuous food grade microemulsion composition established for carotenoids (U.S. patent application Ser. No. 13/534,779, filed Jun. 27, 2012, and incorporated herein in its entirety by this reference) which consists of tween 80:ethanol/limonene:glycerol/$H_2O$. The weight ratio of limonene to ethanol and glycerol to water were fixed at 1:2 and 1:3, respectively. The ratio of oil/surfactant/water used were 32.5/32.5/35 (wt. %) respectively, with 20 wt % of THB monohydrate consisting of polyethoxylated sorbitan ester (Tween 80), water, R-(+)-limonene, ethanol and glycerol, as nano-vehicles. This microemulsion was sprayed on to silica and salt blend to arrive at a dry form of the microemulsion. The maximum inclusion that could be achieved in the final product was about 10%. Hence, the concentration of THB in the final product was 9% considering 90% purity.

Encapsulated THB.

Encapsulated "pearls" of THB were prepared using a pilot scale spray freezer. The THB monohydrate (90% purity, Sigma Aldrich) was used for the production.

Briefly, the vegetable oil was heated at 85° C. until it was completely melted. The liquid oil was then kept at a temperature between 75° C. and 85° C. The vegetable oil was mixed well by a magnetic stirrer and THB was added in small amounts in order to facilitate mixing of the product and to keep the temperature above 75° C. The maximum inclusion of THB that could be achieved in the hydrogenated palm oil matrix was about 30%. The liquid mixture was poured out onto the spinning disk of the spray freeze equipment. The pearls were sieved on a 2000 μm and 600 μm sieve to separate the over and under size product. Considering the purity of the THB (90%) used, the final concentration of THB in the pearls was about 27% (theoretical calculation).

In Vivo Anticoccidial Activity.

The trial was conducted at the R & D poultry farm facility of Kemin Animal Nutrition and Health (India), Gummidipundi. Straight run commercial hybrid broiler chickens, *Gallus domesticus* (Var. Vencobb 400) were used for the study. Day old male chicks were procured from Shanthi hatcheries, Coimbatore, India. Birds were weighed and examined for general health at receipt. The birds were individually identified by wing bands. The chicks were housed in mild steel cages which were cleaned, disinfected using Virkon S (Du Pont, India) and painted earlier. The birds were provided with ad libitum feed and water. No water sanitizers or antimicrobial compounds were used in the water or in the feed. The experimental design is detailed in Table 13. As this was a preliminary study to evaluate the effect of encapsulated and microemulsion of THB in controlling coccidiosis only 2 replicates were maintained.

TABLE 13

Experimental study design for evaluation of in vivo anticoccidial activity. The details of treatment are given in Table 17.

| Category | Trial parameter |
|---|---|
| Duration of trial | 35 days |
| Breed | Cobb 400 |
| Total No. of birds | 240 |
| No. of groups | 11 |
| No. of replicates/group | 2 |
| No. of birds/replicate | 12 (male) |

Farm Management.

The farm and the equipment used for the study were cleaned and disinfected using Virkon S disinfectant (Du Pont, India) by diluting in water at the ratio of 1:200 at the application rate of 1 L/10 m² before the arrival of the chicks. The birds were housed in cages (12 birds/cage) organized on concrete flooring. The temperature and humidity of the farm were monitored continuously using a Hygrometer (TempTec, India) and recorded on daily basis.

Vaccination Schedule.

The birds were vaccinated for Newcastle Disease Virus (NDV) and Infectious Bursal Disease (IBD). The schedule, strain of virus, and route of vaccination are shown in Table 14. The vaccination program was based on the commercial industrial practice in India.

TABLE 14

Vaccination schedule during the trial.

| Vaccine | Dose | Strain of virus | Day | Route |
|---|---|---|---|---|
| IBD | Primary | Intermediate strain# | 10-12 | Intraocular |

\* - NDV vaccine is from MSD, (India)
IBD is from Venky's (India)

Feed Formulation.

A corn soya based mash diet was formulated for the study. The formulation and nutrient composition (calculated using standard values) of the feed are detailed in Tables 15 and 16, respectively.

The feed ingredients were procured from Ponni feeds, Tamil Nadu, India. Three feed formulations were prepared according to the phases of the life of the bird; Prestarter (Day 1-10), Starter (Day 11-21), and Finisher feed (Day 22-35). No antimicrobials and supplements were used in the feed formulation. The products to be evaluated (positive control, Salinomycin and THB) were mixed in the final feed formulation at the corresponding dosages by hand mixing.

TABLE 15

Feed formulation used during the trial.

| Ingredients | Prestarter (kg) | Starter (kg) | Finisher (kg) |
|---|---|---|---|
| Maize | 575 | 602 | 625 |
| Soya meal | 378 | 339 | 302 |
| Rice Bran Oil | 12.5 | 25.5 | 39 |
| Calcite | 16 | 16 | 16 |
| DCP | 11.5 | 10 | 11 |
| Salt | 2.5 | 2.5 | 2.5 |
| Soda Bicarbonate | 1.5 | 1.5 | 1.5 |
| Lysine | 0.5 | 0.7 | 0.7 |
| Methionine | 2.4 | 2.4 | 2.2 |
| Kemzyme PG | 0.1 | 0.1 | 0.1 |
| KemTRACE Broiler | 1 | 1 | 1 |
| Probit plus vitamin | 0.5 | 0.5 | 0.5 |

TABLE 16

Nutrient composition of feed

| Details | Prestarter | Starter | Finisher |
|---|---|---|---|
| Metabolizable Energy (Kcal/Kg) | 2950 | 3050 | 3150 |
| Crude Protein % | 22 | 20.5 | 19 |
| Crude Fat % | 3.9 | 3.8 | 3.6 |
| Ether Extract % | 3.6 | 4.8 | 6.2 |
| Calcium % | 0.98 | 0.95 | 0.95 |
| Average Phosphorus % | 0.48 | 0.45 | 0.45 |
| Lysine % | 1.3 | 1.2 | 1.1 |
| Methionine % | 0.6 | 0.58 | 0.55 |

Details of Treatment Groups.

The birds were fed with either feed containing no anticoccidial agent, THB, encapsulated THB, microemulsion of THB or Salinomycin (Coxistac, Pfizer, India) incorporated in the feed from day 1. Treatment groups and the diet for the groups are given in Table 18. THB was obtained from J P N Pharma, Mumbai, India

TABLE 17

Description of treatment groups. Coccidiosis was induced by oral inoculation of E. maxima oocysts. The treatment agents were given through the feed. Broiler mash feed as shown in Table 3 was used in the study.

| Groups | Treatments |
| --- | --- |
| Control 1 | No infection + feed without anticoccidial |
| Control 2 | Coccidiosis induction + feed without anticoccidial |
| Control 3 | Coccidiosis induction + feed with Coxistac$^$ at 500 g/ton of feed |
| Treatment 1 | Coccidiosis induction + feed with THB at 50 g/ton of feed |
| Treatment 2 | Coccidiosis induction + feed with THB at 75 g/ton of feed |
| Treatment 3 | Coccidiosis induction + feed with encap.* THB 46.3 g/ton of feed (THB conc. 12.5 ppm) |
| Treatment 4 | Coccidiosis induction + feed with encap.* THB at 92.6 g/ton (THB conc. 25 ppm) |
| Treatment 5 | Coccidiosis induction + feed with encap.* THB at 185.2 g/ton (THB conc. 50 ppm) |
| Treatment 6 | Coccidiosis induction + feed with microemul.# of THB at 138.9 g/ton (THB conc. 12.5 ppm) |
| Treatment 7 | Coccidiosis induction + feed with microemul.# of THB at 277.8 g/ton (THB conc. 25 ppm) |
| Treatment 8 | Coccidiosis induction + feed with microemul.# of THB at 416.7 g/ton (THB conc. 37.5 ppm) |

*Encapsulated THB pearls
Microemulsion of THB
$Salinomycin based anticoccidial product from Pfizer
The 12% premix product contains 120 g of Salinomycin/kg; so inclusion of 500 g/ton of feed delivers 60 ppm of active ingredient (recommended dosage).

Oocyst Culture.

The oocysts of E. maxima (isolate ID NKL/11/Ac1) that were maintained at the Department of Veterinary Parasitology, Madras Veterinary College, Chennai were used for the induction of coccidiosis in the trial birds. The origin of the isolate was a broiler bird with clinical coccidiosis, and they were propagated in vivo to yield oocyst quantities sufficient for the study. E. maxima oocysts were cleaned by flotation on a saturated salt solution and treated with 2.5% sodium hypochlorite solution to kill other microbes. The oocyst were washed three times with Phosphate Buffered Saline and sporulated by overnight shaking at 25° C. The sporulated oocysts were enumerated using a Hemocytometer (BS748, Rohem, India) and stored at 4° C. in 2% potassium dichromate solution until further use.

Induction of Coccidiosis.

Sporulated oocysts of E. maxima were inoculated orally gavage to each bird on day 14, 15 and 16 of age at the dosage of $2 \times 10^4$ oocysts/bird/day. Feeding was stopped on the day of inoculation for 2 h before and 2 h after inoculation. Water was not restricted and provided as usual.

Parameters Analyzed.

The parameters that were chosen for analyses were the indices of pathogenesis namely lesion scoring of the midgut for coccidiosis and oocysts per gram (OPG) of excreta per bird.

Lesion scoring. On day 6 of post-infection, 3 birds from each of the replicates were chosen randomly to make a total of 6 birds from each group. Only 3 birds per replicate was chosen for the lesion scoring on day 6 post challenge as the remaining were left for collection of excreta for OPG counts on day 7 and also to observe for mortality due to infection. The birds were sacrificed by cervical dislocation and the intestine was cut open. The scoring was done independently by two qualified veterinarians experienced in lesion scoring for coccidiosis based on Johnson and Reid scoring criteria (Johnson, J. K and W. M. Reid. (1970). Anticoccidial drugs: lesion scoring techniques in battery and floor-pen experiments with chickens. Exp. Parasitol. 28:30-36). The scoring was done double blinded. The score for coccidiosis was a scale of 0 to 4 based on the severity of the lesions in the midgut.

Mean Oocysts/Bird.

Feces from each group were collected separately on day 7 post-challenge as the oocysts peak excretion is observed on the 7$^{th}$ day post challenge (You, M. J. (2014). The comparative analysis of infection pattern and oocyst output in Eimeria tenella, E. maxima and E. acervulina in young broiler chicken. Veterinary World, 7(7): 542-547). The oocyst count was done individually for each cage. Feces collection trays were set up about ½ foot below the cage and fecal droppings of all of the birds were collected from each cage into individual large plastic jars. Fecal droppings in each jar were soaked with an equal amount of water and mixed well using a glass rod. Two 35 ml random samples were taken from each cage. The oocyst count was done individually for each cage. Oocysts were counted microscopically in a McMaster counting chamber using a salt flotation method. The total number of oocysts shed per chicken was calculated using Equation 3.

$$\text{Total} \frac{\text{oocysts}}{\text{bird}} = \frac{\text{oocyst count} \times \text{dilution factor} \times \frac{\text{(fecal sample volume)}}{\text{counting chamber volume}}}{\text{Number of birds per cage}}.$$

Total oocysts shed in the feces of a bird    Equation 3

Statistical Analysis.

Data were analyzed by Analysis of Variance (ANOVA) using Statographics plus software (version 5.1). Statements of statistical significance are declared when $P<0.01$.

Results

Lesion Score.

Figure 27:
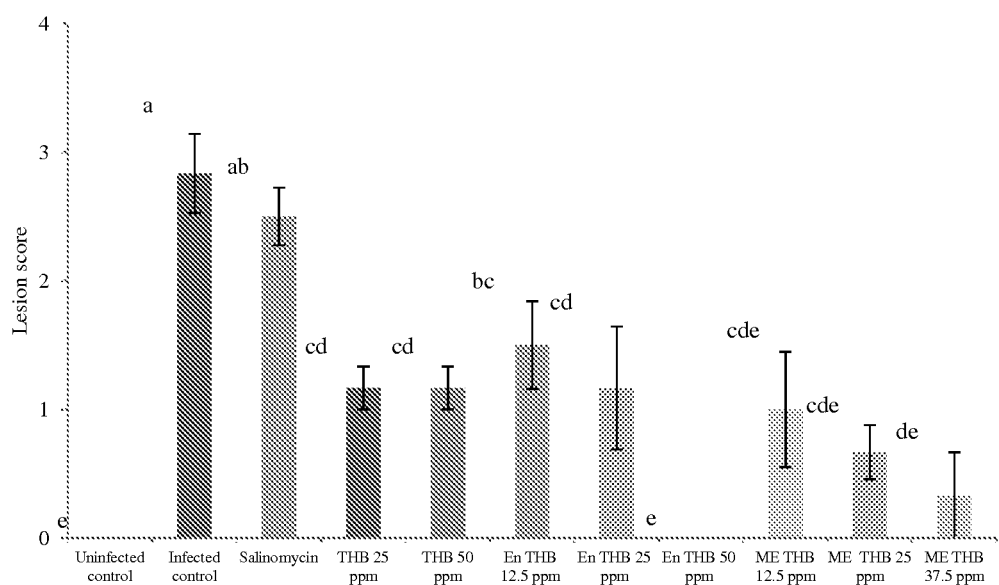
FIG. 27 is a chart of intestinal lesion scores of birds on day 6 post *E. maxima* challenge; the values are expressed average lesion score±SE; columns with different superscripts are statistically significant (P<0.01, n=6).

There were no lesions observed in the uninfected control group, whereas the average lesion score of the infected control was about 2.3 indicating clinical coccidiosis infection. There was no significant reduction in the Salinomycin treated birds ($p>0.01$) as compared to the infected control. All the other supplementations showed significant reduction ($p<0.01$) in the lesions in the mid-gut when compared to the infected control indicating anticoccidial activity. Pure THB at 25 and 50 ppm showed comparable efficacy. The encapsulated THB treated birds showed a dose response trend. Encapsulated THB at 12.5 ppm was comparable to pure THB at 25 ppm. Supplementation of encapsulated THB at 50 ppm reduced the lesions to nil and was significantly ($P<0.01$, FIG. 27) better than all the other groups. No dose response effect was observed with the microemulsion of THB. Supplementation of microemulsion of THB at 12.5 ppm was comparable to 25 and 50 ppm of pure THB.

Mean Oocysts Counts/Bird.

Figure 28:
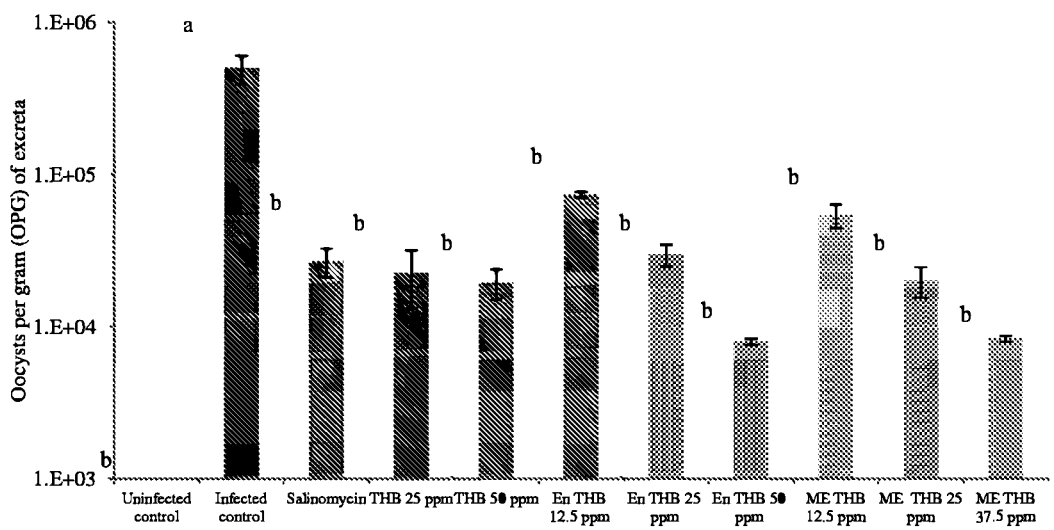
FIG. 28 is a chart of the presence of *Eimeria* oocysts on day 7 post-infection; the values are expressed as number of oocysts/gram/bird±SE; columns with different superscripts are statistically significant (P<0.01, n=4).

The oocysts shedding in the excreta showed that the infected controls had highest oocysts shedding. All other treatment groups showed significant reduction in the oocysts shedding as compared to the infected control ($p<0.01$, FIG. 28). Within the groups, there was no significant difference in the oocysts shedding ($p>0.01$).

Discussion

The infected control had a lesion score close to 3, suggesting that the Eimeria challenge was optimal for the study. The Salinomycin group showed a reduction in lesion scores and this is consistent with the previous observations. THB at both 25 and 50 ppm concentrations showed significant improvement in lesions scores when compared to the positive control. Supplementation of encapsulated THB was found to be more efficacious at lower dosage as compared to the pure THB in this study. A dose dependent response is observed with the encapsulated form of THB, with 12.5 ppm comparable to 25 ppm of pure THB. The better efficacy of the encapsulated THB can be attributed to the sustained and slow release of THB from the lipid matrix. Upon ingestion by the birds, the lipid matrix is acted upon by the lipase in the intestine releasing the active, THB. Earlier studies have reported that THB being a very small molecule of molecular weight 170.1 KD is absorbed readily into the blood stream and the t(max) is about 60 min in rats (Konishi, Y., Hitomi, Y and Yoshioka, E. (2004). Intestinal absorption of p-coumaric and gallic acids in rats after oral administration. J Agric Food Chem. 52(9):2527-32). The retention time of feed in the gastro intestinal tract of the broilers is about 3 hours (Wettstein, D. V., Mikhaylenko, G., Froseth, J. A and Kannangara, C. M (2000). Improved barley broiler feed with transgenic malt containing heat-stable (1,3-1,4)-β-glucanase. Biological Sciences—Applied Biological Sciences, 97 (25): 13512-13517). Hence, slow and sustained release would have maintained the optimum concentration of THB in the lumen for effective action on *E. maxima*. Pure THB on the other hand, would have been absorbed readily requiring higher concentration to achieve a similar efficacy.

Broilers treated with even 12.5 ppm of microemulsion of THB were found to be as efficacious as 25 ppm of pure THB. This also followed a similar pattern as the encapsulated THB. However, a dose dependent effect was not observed. Microemulsions are defined as single optically isotropic and thermodynamically stable solution with droplet sizes in the submicron range. They consist of an oil phase, a surfactant, a co-surfactant, and an aqueous phase. Some advantages offered by microemulsions include improvement in drug solubility, enhancement of bioavailability, protection of the drug against the environment, ease of manufacturing, and a long shelf life (Solanki, S. S., Sarkar, B and Dhanwani, R. K. (2012). Microemulsion Drug Delivery System: For Bioavailability Enhancement of Ampelopsin. ISRN Pharmaceutics, article ID 108164, 4 pages, doi:10.5402/2012/108164).

Example 15—Compatibility of Cozante™ with Tiamulin in Commercial Broilers

COZANTE™ is a novel anticoccidial feed additive containing 3,4,5-trihydroxybenzoicacid as active ingredient. Several anticoccidial agents are incompatible with Tiamulin, one of the widely used anti-mycoplasma drugs in poultry. An in vivo trial was conducted to evaluate the compatibility of COZANTE with Tiamulin in broiler chicken. The trial was conducted for a period of 42 days in Ross 308 males with three treatment groups; treatment 1 supplemented with Tiamulin, treatment 2 with Tiamulin and Coxistac (Salinomycin) and treatment 3 with Tiamulin and COZANTE. The parameters analyzed were body weight gain, feed conversion ratio (FCR), mortality and leg weakness. The results of the study showed that the birds supplemented with Tiamulin and Salinomycin showed lesser weight gain and higher FCR as compared to the Tiamulin treated birds. Whereas, the birds supplemented with Tiamulin and COZANTE showed no reduction in the weight gain and FCR and was comparable to the Tiamulin treated birds. Moreover, the mortality was highest in the group fed with Tiamulin and Salinomycin and lowest in the group fed with Tiamulin and COZANTE. No significant leg weakness was observed in any of the treatment groups. This study clearly indicates that COZANTE is compatible with Tiamulin even at a very high dosage of 1000 g/ton of feed and can be used in combination during the broiler rearing.

COZANTE™ is a novel anticoccidial encapsulated product developed and sold commercially by Kemin Industries, Inc. (Des Moines, Iowa). It is a feed additive and is composed of 3,4,5-trihydroxybenzoic acid (THB) encapsulated in a lipid matrix. This assures the sustained release of THB at the target sites enabling action upon the different species of *Eimeria* that infects the different regions of the gastrointestinal tract (GIT). In vivo trials have shown that COZANTE is able to control coccidiosis in broiler birds in commercial farming conditions. The limitations of the existing anticoccidials like ionophores and chemicals have led to the development of COZANTE. One of the major drawbacks of ionophores is their toxicity in broilers when used in combination with other compounds. One such compound is the anti-mycoplasma drug namely Tiamulin. Even when used at the recommended dosages, the combination of Tiamulin and some of the ionophores result in reduced performance, leg weakness and in severe cases mortality (Laurie, D. (1992). Ionophore toxicity in chickens: a review of pathology and diagnosis. Avian Pathol. 21, 355-368). The recommended dosage of Tiamulin in feed for the prevention of Mycoplasma is 20 ppm in feed throughout the life cycle of the bird. However, the industrial practice in India is the usage of 100 ppm in feed. The aim of the present study was to evaluate the compatibility of COZANTE with Tiamulin in commercial broiler.

Materials and Methods

Experimental facility and study design. An in vivo trial was conducted at Ramadootha poultry farm, Hyderabad, India. Straight run commercial hybrid broiler chickens, *Gallus domesticus* (Var. Ross 308) were used for the study. Day old male chicks were procured from Suguna Broilers, India. The birds were weighed individually, wing banded, and randomly segregated into groups. The experimental design is detailed in Table 18.

TABLE 18

Study design.

| Category | Trial Parameter |
|---|---|
| Rearing type | Deep litter |
| Breed | Ross 308 |
| Sex | Male only |
| Total no of Birds | 432 |
| Number of groups | 3 |
| No of replicates/groups | 8 |
| No. of birds/replicates | 18 |
| Duration of the trial | 42 days |

Farm Management.

Good farm managing practices were followed during the trial (Good farming TNAU AgriTech portal Farm Enterprises. Animal husbandry. http://agritech.tnau.ac.in/farm_enterprises/Farm%20enterprises_%20poultry%20unit.html). The entire farm and the equipment used for the study were cleaned and disinfected before the arrival of the chicks. The temperature and humidity of the farm was monitored continuously. The ideal temperature for the growth of broilers varies throughout the life cycle base on the requirement of the bird ranging from 20 to 34° C. The optimum relative humidity for poultry is 60-80%.

Vaccination Schedule.

The birds were vaccinated for Newcastle Disease Virus (NDV) and Infectious Bursal Disease (IBD). The vaccines used were manufactured by Venkateshwara Hatcheries, Pune, India, and the vaccination was done as per the manufacturer's instruction. The schedule, strain of virus, and route of vaccination were as shown in Table 19.

TABLE 19

Vaccination schedule during the trial.

| Vaccine | Dose | Strain of virus | Vaccination day | Route |
|---|---|---|---|---|
| NDV | Primary | B1 | 5 | Intraocular |
| IBD | Primary | Intermediate strain | 12 | Intraocular |
| NDV | Booster | B1 | 21 | Drinking water |
| IBD | Booster | Intermediate strain | 27 | Drinking water |

Feed formulation. A corn soya based mash diet was formulated, and is shown in Table 20. The mash feed was fed ad libitum to the birds throughout the study period. Three feed formulations were prepared according to the phases of the life of the bird; Prestarter (Day 1-10), Starter (Day 11-20), and Finisher feed (Day 21-42). The nutrient composition of the feed is shown in Table 21.

TABLE 20

Feed formulation used during the trial.

| Ingredients | Prestarter | Starter | Finisher |
|---|---|---|---|
| Maize | 570 | 577 | 620 |
| Soya meal | 378 | 339 | 302 |
| Rice Bran Oil | 12.5 | 25.5 | 39 |
| Calcite | 16 | 16 | 16 |
| DCP expand | 11.5 | 10 | 11 |
| Salt | 2.5 | 2.5 | 2.5 |
| Soda Bicarbonate | 1.5 | 1.5 | 1.5 |
| Lysine | 0.5 | 0.7 | 0.7 |
| Methionine | 2.4 | 2.4 | 2.2 |
| Kemzyme PG | 0.1 | 0.1 | 0.1 |
| Bacitracin Methylene disalicylate (BMD) | 0.5 | 0.5 | 0.5 |

On-top application: KemTRACE Broiler—500 g/ton of feed, Brovit plus vitamin mix—500 g/ton of feed, Toxfin—1000 g/ton of feed

TABLE 21

Nutrient composition of feed

| Details | Prestarter | Starter | Finisher |
|---|---|---|---|
| Metabolizable Energy (Kcal/Kg) | 2950 | 3050 | 3150 |
| Crude Protein % | 22 | 20.5 | 19 |
| Crude Fat % | 3.9 | 3.8 | 3.6 |
| Ether Extract % | 3.6 | 4.8 | 6.2 |
| Calcium % | 0.98 | 0.95 | 0.95 |
| Average Phosphorus % | 0.48 | 0.45 | 0.45 |
| Lysine % | 1.3 | 1.2 | 1.1 |
| Methionine % | 0.6 | 0.58 | 0.55 |

Details of treatment groups. Groups and the treatments are shown in Table 20. The treated birds were fed with supplements incorporated in the feed from day 1 (Table 22).

TABLE 22

Details of treatment groups.

| Groups | Details of the supplementations |
|---|---|
| Treatment 1 | Feed containing Tiamulin FG 10# at 1000 g/ton |
| Treatment 2 | Feed containing Tiamulin FG 10# at 1000 g/ton + Coxistac at 500 g/ton |
| Treatment 3 | Feed containing Tiamulin FG 10# at 1000 g/ton + COZANTE at 75 g/ton |

Tiamulin FG 10 is a Tiamulin product from Dosch Pharmaceuticals; recommended dosage is 200 g/ton but the industry practice in India is 1000 g/ton of feed.
* Coxistac is a product from Pfizer containing Salinomycin at 12% concentration; hence, addition of Coxistac at the mentioned dose of 500 g/ton of feed will enable delivery of Salinomycin at 60 ppm levels in the feed which is the recommended preventive dose for broilers. Treatment groups with COZANTE and Coxistac treatments could not be included in this trial due to limitations in the farm.

Parameters analyzed. The parameters that were chosen for analyses were body weight, feed conversion ratio (FCR) on a weekly basis, mortality and leg weakness on daily basis.

Mean body weight. Birds from each of the groups were removed and weighed individually every week to calculate the weight gain. The cumulative average weight gain of the 8 replicates of each of the group was taken as the mean weight/week.

Feed Conversion ratio (FCR). The total feed consumption was monitored regularly and FCR was arrived at by dividing the feed consumed per bird by the final weight per bird.

Mortality. Mortality was recorded on daily basis and the total mortality was calculated and expressed as %. Post mortem analysis was performed for the dead birds by trained veterinarians to elucidate the reason for the death.

Leg weakness. All birds were examined every day for the major clinical signs, leg weakness which was scored on a 0 to 4 scale. The criteria for the scoring were as given below (Stipkovits, L., Salyi, G., Glavits, R and Burch, D. G. S. (1999). Testing the compatibility of a combination of tiamulin/chlortetracycline 1:3 premix (Tetramutin-Novartis) given in feed at different levels with salinomycin in chickens. Avian Pathology, 28, 579-586).

Score 0—no signs,

Score 1—slow movement, infrequent sitting,

Score 2—ataxia, difficult movement, frequent sitting, slight abnormality in feathers Score 3—absence of movement, lack of appetite, significant changes in feathers, paresis or paralysis Statistical analysis. Data were analyzed by Analysis of Variance using Statographics plus software (version 5.1). Statements of statistical significance are declared when $P<0.01$.

Results

Temperature and humidity. Temperature of the farm ranged from 22.06 to 35.16° C. and the humidity from 43 to 86.29% over the 6 weeks trial period.

Figure 29:
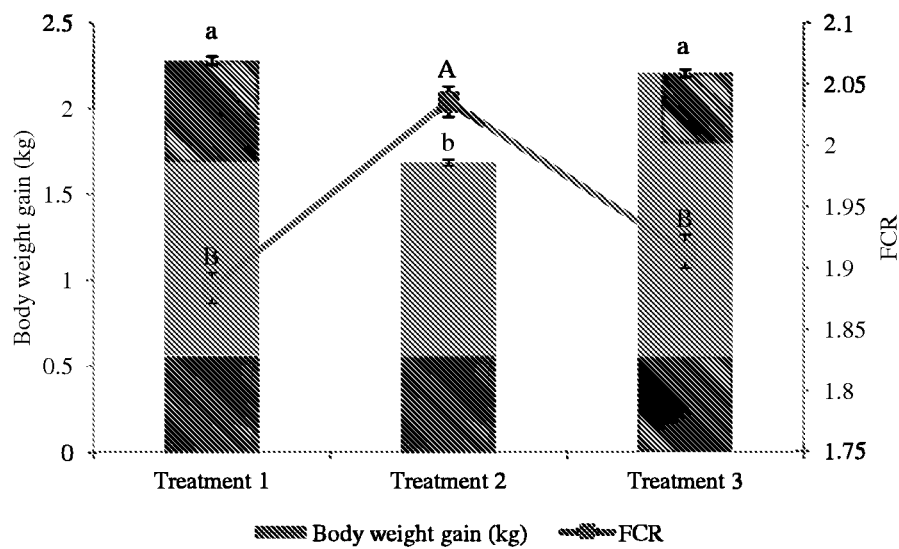
FIG. 29 is a chart of the body weight gain and FCR of birds of different treatment groups. Treatment 1–Tiamulin, Treatment 2–Tiamulin+Coxistac, Treatment 3–Tiamulin+COZANTE. Columns with different superscripts are statistically significant (p<0.01, n=8).

Body weight gain and FCR. Birds supplemented with Coxistac (Salinomycin) along with Tiamulin showed significantly reduced body weight and higher FCR as compared to the Tiamulin group ($p<0.01$, FIG. 29). But, the group treated with Tiamulin and COZANTE did not show any reduction in the growth performance and was comparable to the Tiamulin group.

Figure 30:
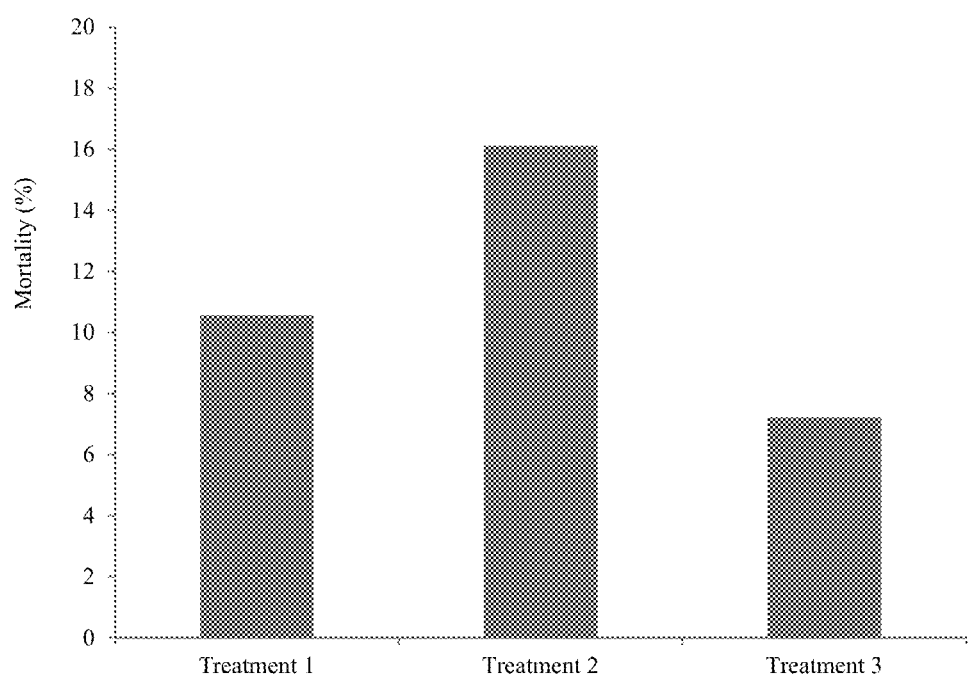
FIG. 30 is a chart of the mortality of the different treatment groups at the end of 6 weeks. Treatment 1–Tiamulin, Treatment 2–Tiamulin+Coxistac, Treatment 3–Tiamulin+COZANTE.
Figure 31A:
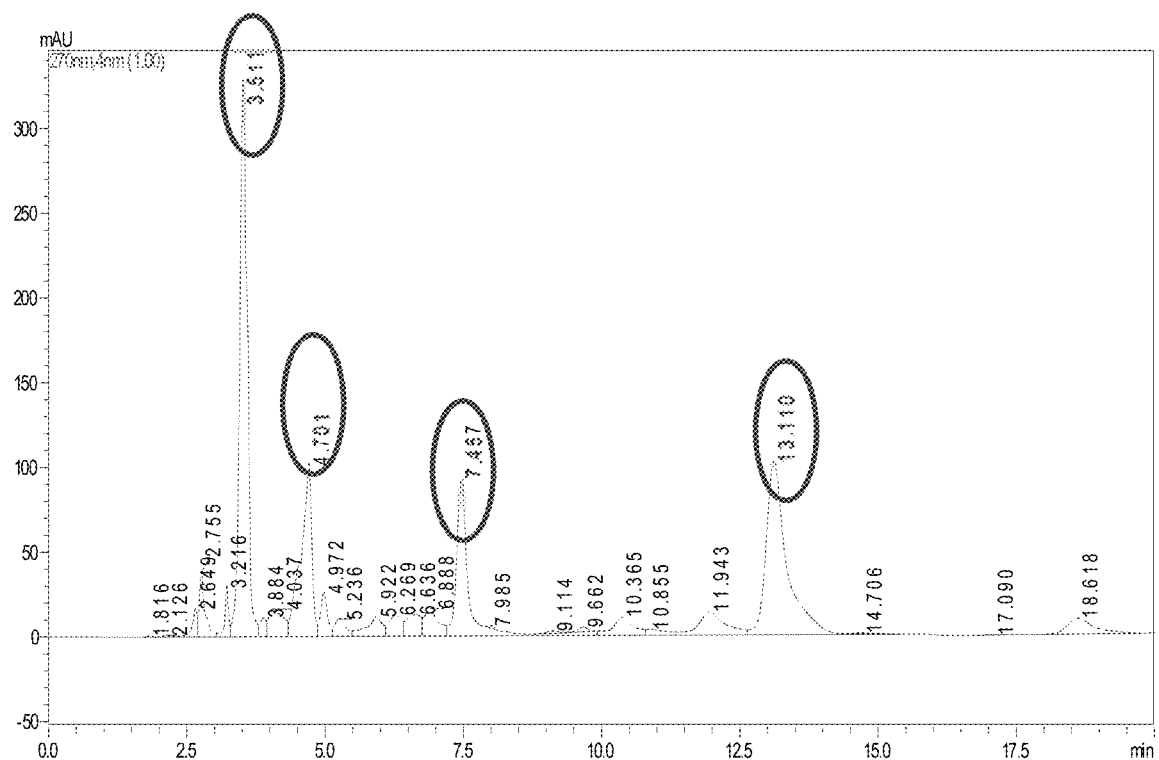
FIG. 31a is a chromatogram of a water extract of gallnut showing four distinct peaks and FIG. 31b is a chromatogram of standard gallic acid (Sigma Aldrich, India, 100 ppm).
Figure 31B:
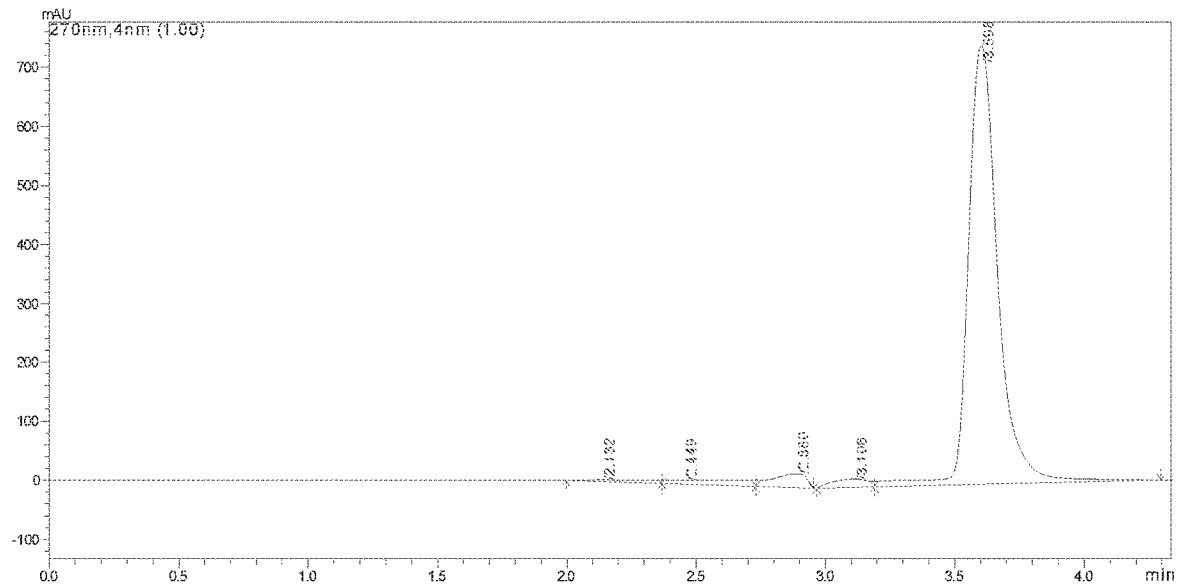
Figure 32:
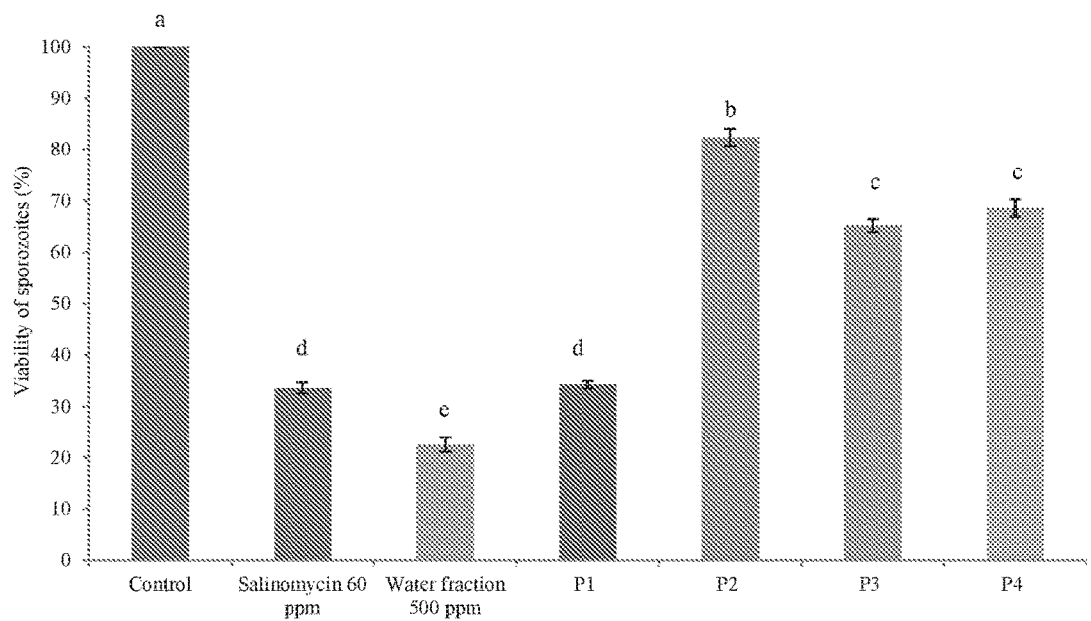
FIG. 32 is a chart of the in vitro anti-sporozoite activity of the different peaks of water fraction of gall nuts. The individual compounds/peaks (P1-P4) were tested at the proportion that they are present in the water fraction as determined by the analytical HPLC area peak. n=3, p<0.05
Figure 33:
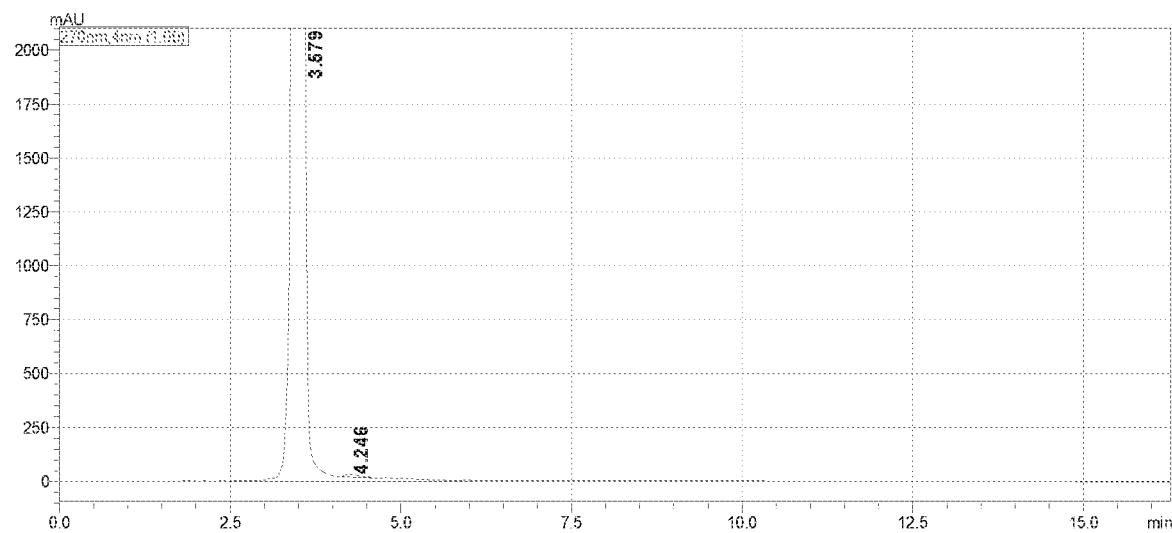
FIG. 33 is a chart of the LCMS chromatogram of peak 1 of water fraction of gallnut.
Figure 34:
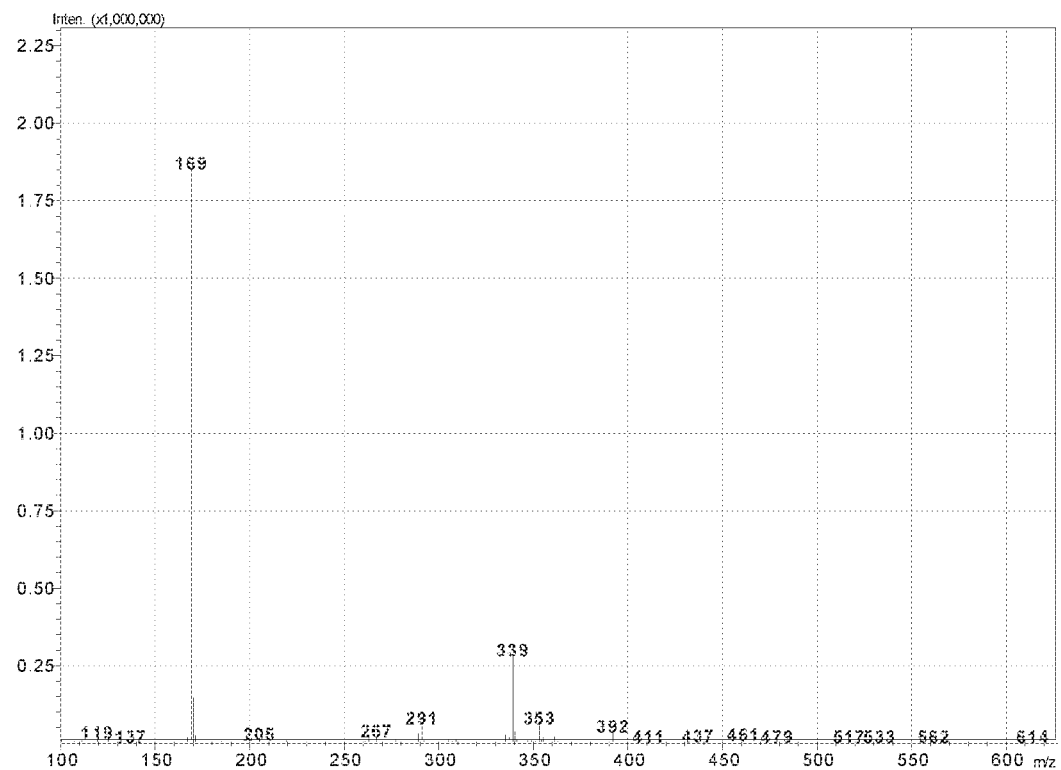
FIG. 34 is a chart of the LCMS Spectrum of Peak 1 of water fraction of gallnut.
Figure 35:
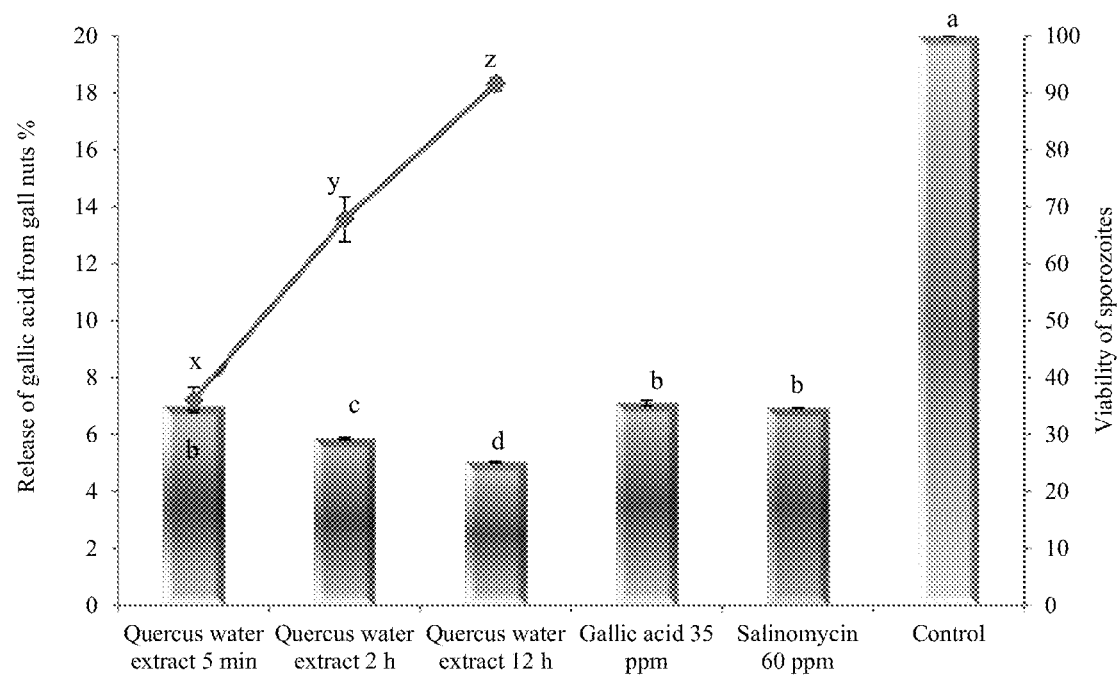
FIG. 35 is a chart of the anti-sporozoite activity of gallic acid versus the water extract of gallnut; n=3, p<0.05.

Mortality (%). The birds supplemented with Tiamulin and Coxistac (Salinomycin) showed highest mortality and Tiamulin+COZANTE supplementation showed lowest mortality as compared to the Tiamulin group. Mortality rate is given in FIG. 30.

Leg weakness. No cases of prominent leg weak were observed in any of the groups despite usage of very high dosage of Tiamulin.

Discussion

Toxicity of ionophore when used in combination with Tiamulin is well reported. Most of the ionophores including Monensin, Salinomycin, Semduramicin, narasin have been reported to incompatible with Tiamulin (Laurie, et al., 1992; Schuhmacher, A. K., Bafundo, W., Islam, K. M. S., Aupperle, H., Glaser, R., Schoon, H. A and Gropp, J. M. (2006). Tiamulin and Semduramicin: Effects of simultaneous administration on performance and health of Growing Broiler Chickens. Poult. Sci. 85:441-445. Tiamulin can induce and directly inhibit CYP3A enzymes, which are predominantly responsible for monensin 0-demethylation (Islam, K. M. S., Klein, U and Burch, D. G. S. (2009). The activity and compatibility of the antibiotic tiamulin with other drugs in poultry medicine—A review. Poult. Sci. 88:2353-2359). This results to accumulation of monensin in the blood leading to ionophore toxicity. Clinically, signs include incoordination, leg weakness, diarrhea, reduced feed intake and weight depression. Gross lesions of monensin toxicity include emaciation, generalized congestion, myocardial enlargement and pallor, ascites and hydropericardium. The most common lesions were myocardial streaking and pallor, dilatation of the ventricles of the heart and lack of myocardial tone (Szucsa, G., Tamasib, V., Laczayc, P and Monostroy, K. (2004). Biochemical and background of toxic interaction between tiamulin and monensin. Chemico-biological interactions. 147 (2):151-161).

Despite using higher levels of Tiamulin (1000 g/ton of feed) as against the recommended dosage, there was no leg weakness or mortality associated with toxicity in any of the treatment groups. Total mortality observed in the different treatment groups were attributed to Necrotic Enteritis (NE) infection in the farm by post mortem analysis. The lowest mortality in the COZANTE treated birds could be due to effect of COZANTE in controlling coccidiosis, as coccidiosis is a predisposing factor for Clostridium perfringens causing NE (Shojadoost, B., Vince, A. R and Prescott, J. F (2012). The successful experimental induction of necrotic enteritis in chickens by Clostridium perfringens: a critical review. Veterinary Research, 43:74).

Reduction in body weight gain and increase in FCR in the birds supplemented with Tiamulin and Salinomycin indicates interaction. This is attributable to the incompatibility of Tiamulin and Salinomycin proven by earlier studies indicating that incompatibility leads to reduction in performance, muscular alterations and even death in severe cases (Laurie, et al., 1994; Szucsa, et al., 2004; Dowling, L. (1992). Ionophore toxicity in chickens: A review of pathology and diagnosis, Avian Pathology, 21(3), 355-368; Vieira, S. L., Favero, A., Berres, J., Freitas, D. M., Martinez, J. E. P., Mayorga, M. E and Coneglian, J. L. B. (2010). Live performance and processing yields of broilers fed diets with tiamulin and salinomycin combinations Rev. Bras. Cienc. Avic. 12 (1): 35-39; Islam, K. M., Afrin, S., Das, P. M., Hassan, M. M., Valks, M., Klein, U., Burch, D. G and Kemppainen, B. W. (2008). Compatibility of a combination of tiamulin and chlortetracycline with salinomycin in feed during a pulsed medication program co-administration in broilers. Poult Sci. 87(12):2528-34). The absence of mortality and leg weakness along with the performance reduction indicates mild toxicity (Islam, et al., 2009). The birds treated with Tiamulin+COZANTE did not show any reduction in performance indicating no observable adverse effects when used in combination. This clearly shows that COZANTE is compatible with Tiamulin and can be used in combination in broilers. This overcomes the existing issue related to the incompatibility of Tiamulin and Ionophore encouraging the use of COZANTE to control coccidiosis and Tiamulin to control Mycooplasma.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A method of controlling coccidiosis in animals, comprising the step of administering a plant extract to the animal, said plant extract from a plant selected from the group consisting of *Quercus infectoria* and *Rhus chinensis*, said plant extract being administered to the animals in a dose of at least 10 ppm.

2. The method of claim 1, wherein the plant extract is administered to the animals in a dose of from about 12.5 to 50 ppm.

3. The method of claim 1, wherein the plant extract is administered in combination with an anti-*mycoplasma* drug without observable adverse effects.

4. The method of claim 1, wherein the coccidiosis is caused by *Eimeria* spp.

5. The method of claim 4, wherein the *Eimeria* spp. are selected from the group consisting of *E. tenella, E. maxima* and *E. acervulina*.

6. The method of claim 1, wherein controlling coccidiosis includes a reduction in lesion score, oocysts per gram of fecal matter or mortality.

7. A method of controlling coccidiosis in animals, comprising the step of administering a microemulsion, wherein the microemulsion comprises a plant extract, and wherein the plant extract is from a plant selected from the group consisting of *Quercus infectoria* and *Rhus chinensis*, said plant extract being administered to the animals in a dose of at least 10 ppm.

8. The method of claim 7, wherein the plant extract is administered in a dose of from 12.5 to 50 ppm.

9. The method of claim 7, wherein the microemulsion is administered in combination with an anti-*mycoplasma* drug without observable adverse effects.

10. The method of claim 7, wherein the coccidiosis is caused by *Eimeria* spp.

11. The method of claim 10, wherein the *Eimeria* spp. are selected from the group consisting of *E. tenella, E. maxima* and *E. acervulina*.

12. The method of claim 7, wherein controlling coccidiosis includes a reduction in lesion score, oocysts per gram of fecal matter or mortality.

* * * * *